US008779214B2

(12) United States Patent  
Barnicki et al.

(10) Patent No.: US 8,779,214 B2
(45) Date of Patent: Jul. 15, 2014

(54) METHODS FOR RECOVERY AND RECYCLE OF RUTHENIUM HOMOGENOUS CATALYSTS

(71) Applicant: Eastman Chemical Company, Kingsport, TN (US)

(72) Inventors: Scott Donald Barnicki, Kingsport, TN (US); Jeffrey Scott Kanel, Kingsport, TN (US); Kenneth Wayne Hampton, Jr., Glimer, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 13/896,706

(22) Filed: May 17, 2013

(65) Prior Publication Data

US 2013/0253232 A1 Sep. 26, 2013

Related U.S. Application Data

(62) Division of application No. 12/889,065, filed on Sep. 23, 2010, now Pat. No. 8,466,328.

(60) Provisional application No. 61/374,850, filed on Aug. 18, 2010.

(51) Int. Cl.
*C07C 27/04* (2006.01)

(52) U.S. Cl.
USPC .......................................... 568/864; 568/868

(58) Field of Classification Search
None
See application file for complete search history.

(56) References Cited

U.S. PATENT DOCUMENTS

| 2,152,852 A | 4/1939 | Loder |
|---|---|---|
| 2,153,064 A | 4/1939 | Larson |
| 2,211,624 A | 8/1940 | Loder et al. |
| 2,211,625 A | 8/1940 | Loder |
| 2,298,138 A | 10/1942 | Loder |
| 2,436,209 A | 2/1948 | Elgin |
| 2,443,482 A | 6/1948 | Shattuck |
| 3,333,924 A | 8/1967 | Hazen et al. |
| 3,751,453 A | 8/1973 | Kurkov et al. |
| 3,754,028 A | 8/1973 | Lapporte et al. |
| 3,801,627 A | 4/1974 | Kurkov et al. |
| 3,859,349 A | 1/1975 | Cody |
| 3,911,003 A | 10/1975 | Suzuki |
| 3,927,078 A | 12/1975 | Lapporte et al. |
| 3,948,977 A | 4/1976 | Suzuki |
| 3,948,986 A | 4/1976 | Suzuki |
| 4,016,208 A | 4/1977 | Suzuki |
| 4,052,452 A | 10/1977 | Scardigno et al. |
| 4,087,470 A | 5/1978 | Suzuki |
| 4,112,245 A | 9/1978 | Zehner et al. |
| 4,128,575 A | 12/1978 | Leupold et al. |
| 4,136,112 A | 1/1979 | Bakshi |
| 4,140,866 A | 2/1979 | Nielsen |
| 4,153,809 A | 5/1979 | Suzuki |
| 4,228,305 A | 10/1980 | Suzuki |
| 4,275,234 A | 6/1981 | Baniel et al. |
| 4,291,007 A | 9/1981 | Baniel |
| 4,308,397 A | 12/1981 | Suzuki |
| 4,366,333 A | 12/1982 | Wilkes |
| 4,409,395 A | 10/1983 | Miyazaki et al. |
| 4,431,486 A | 2/1984 | Balmat |
| 4,440,734 A | 4/1984 | Kougioumoutzakis |
| 4,501,917 A | 2/1985 | Schmidt et al. |
| 4,691,048 A | 9/1987 | Hughes et al. |
| 4,824,997 A | 4/1989 | Macfarlane et al. |
| 4,935,102 A | 6/1990 | Berg |
| 4,966,658 A | 10/1990 | Berg |
| 4,990,629 A | 2/1991 | Souma |
| 5,026,927 A | 6/1991 | Andrews et al. |
| 5,210,335 A | 5/1993 | Schuster et al. |
| 5,214,219 A | 5/1993 | Casale et al. |
| 5,276,181 A | 1/1994 | Casale et al. |
| 5,423,955 A | 6/1995 | Berg |
| 5,455,372 A | 10/1995 | Hirai et al. |
| 5,723,662 A | 3/1998 | Ebmeyer et al. |
| 5,932,772 A | 8/1999 | Argyropoulos et al. |
| 5,952,530 A | 9/1999 | Argyropoulos et al. |
| 6,252,121 B1 | 6/2001 | Argyropoulos et al. |

(Continued)

FOREIGN PATENT DOCUMENTS

| DE | 3133353 C2 | 3/1983 |
|---|---|---|
| EP | 0 114 657 B1 | 3/1987 |

(Continued)

OTHER PUBLICATIONS

Notice of Transmittal of the International Search Report and the Written Opinion of the International Search Authority with Mail Date of Mar. 15, 2012 for International Application No. PCT/US2011/0151490.

Notice of Transmittal of the International Search Report and the Written Opinion of the International Search Authority with Mail Date of Nov. 28, 2011 for International Application No. PCT/US2011/047842.

Notice of Transmittal of the International Search Report and the Written Opinion of the International Search Authority with Mail Date of Aug. 13, 2013 for International Application No. PCT/US2013/033458.

(Continued)

*Primary Examiner* — Sudhakar Katakam

(74) *Attorney, Agent, or Firm* — Jennifer R. Knight; Eric Middlemas

(57) ABSTRACT

Disclosed is a process for the extractive recovery of a homogeneous ruthenium catalyst from the reaction product of the hydrogenation of glycolic acid, glycolate esters, and/or glycolic acid oligomers with an extractant comprising a hydrophobic solvent and an optional hydrophilic solvent. The ruthenium catalyst, which can include 1,1,1-tris(diaryl- or dialkylphosphinomethyl)alkane ligands, can be recovered from the hydrophobic extract phase by back extraction with a hydrophilic solvent and recycled to a process for the preparation of ethylene glycol by the hydrogenation of glycolic acid and glycolic acid derivatives.

8 Claims, 4 Drawing Sheets

(56) References Cited

U.S. PATENT DOCUMENTS

| | | | |
|---|---|---|---|
| 6,291,725 B1 | 9/2001 | Chopade et al. | |
| 6,294,700 B1 | 9/2001 | Kanel et al. | |
| 6,303,829 B1 | 10/2001 | Kanel et al. | |
| 6,307,108 B1 | 10/2001 | Argyropoulos et al. | |
| 6,307,109 B1 | 10/2001 | Kanel et al. | |
| 6,307,110 B1 | 10/2001 | Argyropoulos et al. | |
| 6,310,260 B1 | 10/2001 | Argyropoulos et al. | |
| 6,376,723 B2 | 4/2002 | Drent et al. | |
| 7,056,439 B2 | 6/2006 | Baniel et al. | |
| 7,122,698 B2 | 10/2006 | Yoshida et al. | |
| 7,164,040 B2 | 1/2007 | Kuroda et al. | |
| 7,223,885 B2 | 5/2007 | Van Krieken | |
| 7,439,391 B2 | 10/2008 | Gallagher et al. | |
| 7,615,671 B2 * | 11/2009 | Puckette et al. | 568/864 |
| 7,709,689 B2 * | 5/2010 | Kilner et al. | 568/885 |
| 7,772,423 B2 | 8/2010 | Celik et al. | |
| 8,466,328 B2 * | 6/2013 | Barnicki et al. | 568/864 |
| 2004/0222153 A1 | 11/2004 | Baniel et al. | |
| 2006/0160197 A1 | 7/2006 | Li et al. | |
| 2007/0123739 A1 | 5/2007 | Crabtree et al. | |
| 2008/0275277 A1 | 11/2008 | Kalagias | |
| 2009/0143612 A1 | 6/2009 | Puckette et al. | |
| 2011/0144388 A1 | 6/2011 | Sun et al. | |
| 2011/0166383 A1 | 7/2011 | Sun et al. | |
| 2012/0046481 A1 | 2/2012 | Barnicki et al. | |
| 2012/0046500 A1 | 2/2012 | Barnicki et al. | |
| 2012/0078010 A1 | 3/2012 | Barnicki et al. | |
| 2012/0184783 A1 | 7/2012 | Barnicki et al. | |

FOREIGN PATENT DOCUMENTS

| | | |
|---|---|---|
| EP | 0 676 239 A2 | 10/1995 |
| EP | 1 679 331 A1 | 7/2006 |
| GB | 508383 A | 6/1939 |
| GB | 1499245 A | 1/1978 |
| GB | 2179337 A | 7/1986 |
| IL | 89044 A | 3/1993 |
| JP | 56100741 A | 8/1981 |
| JP | 56131546 A | 10/1981 |
| JP | 56133237 A | 10/1981 |
| JP | 5746934 A | 3/1982 |
| JP | 57040442 A | 3/1982 |
| JP | 57102837 A | 6/1982 |
| JP | 6228045 A | 8/1994 |
| JP | 1999147042 A | 6/1999 |
| JP | 2004131411 A | 4/2004 |
| RU | 1436453 A1 | 9/1996 |
| WO | 97/15543 A1 | 5/1997 |
| WO | 2006/069127 A1 | 6/2006 |
| WO | 2009/140850 A1 | 11/2009 |
| WO | 2012/040007 A2 | 3/2012 |
| WO | 2012/130316 A1 | 10/2012 |

OTHER PUBLICATIONS

Notice of Transmittal of the International Search Report and the Written Opinion of the International Search Authority with Mail Date of Jun. 25, 2013 for International Application No. PCT/US2013/033501.

Notice of Transmittal of the International Search Report and the Written Opinion of the International Search Authority with Mail Date of Aug. 16, 2013 for International Application No. PCT/US2013/033410.

Notice of Transmittal of the International Search Report and the Written Opinion of the International Search Authority with Mail Date of Jun. 21, 2013 for International Application No. PCT/US2013/033520.

Notice of Transmittal of the International Search Report and the Written Opinion of the International Search Authority with Mail Date of Jun. 21, 2013 for International Application No. PCT/US2013/033411.

Notice of Transmittal of the International Search Report and the Written Opinion of the International Search Authority with Mail Date of Jul. 8, 2013 for International Application No. PCT/US2013/033494.

Notice of Transmittal of the International Search Report and the Written Opinion of the International Search Authority with Mail Date of Jul. 12, 2013 for International Application No. PCT/US2013/033446.

Celik et al., "Synthesis of precursors to ethylene glycol from formaldehyde and methyl formate catalyzed by heteropoly acids", Journal of Molecular Catalysis A: Chemical 288, (2008), pp. 87-96.

Celik et al., "Vapor-phase carbonylation of dimethoxymethane of H-Faujasite", Angewandte. Chemie Int. Ed. 2009, 48, pp. 4813-4815.

Hou-Yong, Sun, et al. "Reactive extraction of glycolic acid in high content solution with tri-n-octylamine" Journal of Chemical Engineering of Chinese Universities, Feb. 2007, vol. 21 pp. 26-30.

Asci, Yavuz Selim et al. "Extraction of Glycolic Acid from Aqueous Solutions by Amberlite LA-2 in Difference Diluent Solvents" J. Chem Eng. Data 2009, 54, 2791-2794.

Bizek, Vladislav et al. "Amine Extraction of Hydroxycarboxylic Acids. 1. Extraction of Citric Acid with 1-Octanol/n-Heptane Solutions of Trialkylamine" Ind. Eng. Chem. Res. 1992, 31, 1554-1562.

Tamada, Janet A. et al. "Extraction of Carboxylic Acids with Amine Extractants. 1. Equilibria and Law of Mass Action Modeling" Ind. Eng. Chem. Res. 1990, 29, 1319-1326.

Smith, E. Lester, et al., "The Acid-Binding Properties of Long-Chain Aliphatic Amines", J.S.C.I., 67, Feb. 1948 pp. 48-51.

Walker, "Formaldehyde", ACS Monograph, Washington, DC., (1964), p. 95.

Eyal, A., et al. "Recovery and Concentration of Strong Mineral Acids from Dilute Solutions Through LLX III. A "Temperature Swing" Based Process", Solvent Extraction and Ion Exchange, 9 (2), pp. 223-236 (1991).

Eyal, A.M., et al. "Recovery and Concentration of Strong Mineral Acids from Dilute Solutions Through LLX. I: Review of Parameters for Adjusting Extractant Properties and Analysis of Process Options", Solvent Extraction and Ion Exchange, 9 (2), pp. 195-210 (1991).

Eyal, A.M., et al. "Recovery and Concentration of Strong Mineral Acids from Dilute Solutions Through LLX. II. Reversible Extraction with Branched-Chain Amines", Solvent Extraction and Ion Exchange, 9(2), pp. 211-222 (1991).

Eyal, Aharon, et al. "Extraction of Strong Mineral Acids by Organic Acid-Base Couples", Ind. Eng. Chem. Process Des. Dev., (1982), vol. 21, No. 2, pp. 334-337.

Handbook of Solvent Extraction, Krieger Publishing Company, Malabar, FL, 1991, pp. 275-501.

Treybal, Robert E. "Methods of Calculation II. Stagewise Contact, Multicomponent Systems", Liquid Extraction, $2^{nd}$ Edition, McGraw-Hill Book Company, New York. 1963, pp. 275-276.

Treybal, Robert E., Liquid Extraction $2^{nd}$ Ed., McGraw-Hill Book Company, New York, NY, 1963, pp. 349-366.

Gerberich, H. Robert et al., "Formaldehyde", Kirk-Othmer Encyclopedia of Chemical Technology, vol. 11, $4^{th}$ Edition, 1994, pp. 929-951.

Treybal, Robert E., Liquid Extraction, $2^{nd}$ Ed., McGraw Hill Book Company, 1963, pp. 248-252.

Lynch, Kathleen M., et al., "Improved Preparations of 3-Chloro-2(chloromethyl)-1-propene and 1,1-Dibromo-2,2-bis(chloromethyl)-cyclopropane: Intermediates in the Synthesis of [1.1.1]Propellane", J. Org. Chem, 60, (1995), pp. 4666-4668.

"Tray Design and Operation", Distillation Design, McGraw-Hill, New York (1992), Chapter 6, pp. 259-263.

"Packing Design and Operation", Distillation Design, McGraw-Hill, New York, (1992), Chapter 8, pp. 421-521.

Seader, J.D., Ph.D, et al., "Distillation", Perry's Handbook of Chemical Engineering, Section 13, $7^{th}$ Ed., McGraw-Hill Book Co. 1999.

Lee, Sang Young, et al., "Carbonylation of Formaldehyde over Ion Exchange Resine Catalysts. 1. Batch Reactor Studies", Ind. Eng. Chem. Res., 32, (1993), pp. 253-259.

Xu, Qiang, et al., "Preparation and Catalytic Application of Cationic Metal Carbonyls", Science and Technology in Catalysis, (2002), pp. 215-218.

Xu, Qiang, "Metal carbonyl cations: generation, characterization and catalytic application", Coordination Chemistry Reviews, 231, (2002), pp. 83-108.

(56) References Cited

OTHER PUBLICATIONS

Suzuki, S., et al., "Ethylene Glycol from Methanol and Synthesis Gas via Glycolic Acid", Catalytic Converstions of Synthesis Gas and Alcohols to Chemicals, (1984). pp. 221-247.
Wang, Zheng Bao, et al., Carbonylation of Formaldehyde with Carbon Monoxide over Cation-Exchange Resin Catalysts, Bull. Chem. Soc. Jpn., 72, (1999), pp. 1935-1940.
Sano, Tsunejo, et al., "Synthesis of 1,3-dioxolan-4-one from trioxane and carbon monoxide on HZSM-5 zeolite", Chem. Community, (1997), pp. 1827-1828.
Souma, Yoshie, "Carbonylation at Ambient Pressure in Strong Acids", Journal of Synthetic Organic Chemistry, vol. 47, No. 6, (1983), pp. 561-569.
Soma, Yoshie, et al., "Normal-Pressure CO Addition Reaction of Formaldehyde and Related Compounds on Copper Carbonyl Catalyst", Catalyst 23, (1981), pp. 48-50.
Li, Tao, et al., "Carbonylation of formaldehyde catalyzed by p-toluenesulfonic acid", Catalysis Today, 111, (2006), pp. 288-291.
Souma, Yoshie, et al., "Synthesis of tert.-Alkanoic acid catalyzed by $Cu(CO)^+_n$ and $Ag(CO)^+_2$ under atmospheric pressure", Catalysis Today, 36, (1997), pp. 91-97.
Hendriksen, Dan E., "Intermediates to Ethylene Glycol: Carbonylation of Formaldehyde Catalyzed by NAFION Solid Perfluorosulfonic Acid Resin", Prep. A.C.S. Div. Fuel Chem., 28, (1983), pp. 176-190.
Bhattacharyya, S.K., et al., "High-Pressure Synthesis of Glycolic Acid from Formaldehyde, Carbon Monoxide, and Water in Presence of Nickel, Cobalt, and Iron Catalysts", Advanced Catalysts, 9, (1957), pp. 625-635.
Baniel, A., et al., "Acid-Base Couple Solvents in Recovery of Mineral Acids From Waste Streams", Proceedings of $2^{nd}$ International Conference on Separations Science and Technology, Oct. 1-4, 1989, pp. 667-674.
Wegescheider, Rud., et al., "Addition of Acid Anhydrides to Aldehydes and Ketones", Royal and Imperial University of Vienna, presented at the meeting of Nov. 4, 1909, pp. 1-47.
King, Walter D., et al. "The Acid-Catalyzed Reaction of Acetic Anhydride with Some Oxocanes", Journal of Applied Polymer Science, vol. 18, (1974) pp. 547-554.
He, Dehua, et al., "Condensation of formaldehyde and methyl formate to methyl glycolate and methyl methoxy acetate using heteropolyacids and their salts", Catalysis Today, 51, (1999), pp. 127-134.

Co-pending U.S. Appl. No. 12/889,045, filed Sep. 23, 2010, Scott Donald Barnicki, et al.
Co-pending U.S. Appl. No. 12/889,065, filed Sep. 23, 2010, Scott Donald Barnicki, et al.
Co-pending U.S. Appl. No. 13/431,335, filed Mar. 27, 2012, Scott Donald Barnicki, et al.
Co-pending U.S. Appl. No. 13/431,358, filed Mar. 27, 2012, Scott Donald Barnicki, et al.
Co-pending U.S. Appl. No. 13/431,369, filed Mar. 27, 2012, Scott Donald Barnicki, et al.
Co-pending U.S. Appl. No. 13/431,402, filed Mar. 27, 2012, Scott Donald Barnicki, et al.
Co-pending U.S. Appl. No. 13/431,386, filed Mar. 27, 2012, Scott Donald Barnicki, et al.
Co-pending U.S. Appl. No. 13/491,954, filed Jun. 8, 2012, Mesfin Ejerssa Janka.
Notice of Allowance for U.S. Appl. No. 12/889,045 dated Jul. 18, 2012.
Notice of Allowance for U.S. Appl. No. 12/889,065 dated Oct. 15, 2012.
Malinowski, J.J. "Evaluation of Liquid Extraction Potentials for Downstream Separation of 1,3-Propanediol", Biotechnology Techniques, vol. 18, No. 2 (Jan. 1, 1999), pp. 127-130.
Cox et al. "Mechanistic Studies in Strong Acids . . . ", Journal of Organic Chemistry, vol. 51, No. 19 (Sep. 1, 1986), pp. 3619-3624.
Li et al. "Aqueous Two-phase Extraction of 1,3-propanediol from Glycerol-based Fermentation Broths", Separation and Purification Technology Separation and Purification Technology, vol. 66, No. 3 (May 7, 2009), pp. 472-478.
Office Action dated Jul. 18, 2013 for U.S. Appl. No. 13/431,386.
Notice of Allowance for U.S. Appl. No. 13/431,358 dated Aug. 2, 2013.
Notice of Allowance for U.S. Appl. No. 12/889,045 dated Sep. 19, 2013.
USPTO Office Action for U.S. Appl. No. 13/431,358 dated Nov. 12, 2013.
USPTO Office Action (Election/Restriction Requirement) dated Nov. 18, 2013 for U.S. Appl. No. 13/431,335.
USPTO Notice of Allowance dated Dec. 3, 2013 for U.S. Appl. No. 13/431,386.
USPTO Notice of Allowance dated Dec. 13, 2013 for U.S. Appl. No. 13/889,045.
USPTO Office Action dated Jan. 13, 2014 for U.S. Appl. No. 13/431,369.

* cited by examiner

METHODS FOR RECOVERY AND RECYCLE OF RUTHENIUM HOMOGENOUS CATALYSTS

CROSS REFERENCES TO RELATED APPLICATIONS

This application is a divisional application of co-pending U.S. Non-Provisional application Ser. No. 12/889,065, filed on Sep. 23, 2010, which claims the benefit of U.S. Provisional Application Ser. No. 61/374,850, filed Aug. 18, 2010, both of which are incorporated herein by reference in their entirety.

FIELD OF THE INVENTION

The invention generally relates to a process for separation of homogeneous catalysts from the reaction products of the hydrogenation of 1,2-dioxygenated organic compounds. More specifically, this invention relates to a process for the extractive recovery of a catalyst composition comprising ruthenium and a 1,1,1-tris(diaryl- or dialkylphosphinomethyl)alkane from a glycolic acid hydrogenation product. The recovered catalyst system may be recycled to a process for the hydrogenation of glycolic acid and/or derivatives thereof.

BACKGROUND OF THE INVENTION

Homogeneous ruthenium—phosphine catalysts are useful for the reduction of 1,2-dioxygenated organic compounds, such as alkyl oxalates, glycolic acid, and glycolate esters to ethylene glycol. In particular, catalysts containing ruthenium in combination with tridentate phosphorus ligands such as, for example, tris-1,1,1-(diphenylphosphino-methyl)ethane (also known as "triphos"), have been used for the reduction of glycolic acid to ethylene glycol. These catalyst systems, however, are expensive and their economical use requires efficient recovery of the metal and ligand from the reaction products.

Many metal-organophosphorus ligand catalysts are known to be sensitive to the composition of the gaseous phase above the catalyst reaction medium and to temperature. For example, the recovery of rhodium-phosphine hydroformylation catalysts often involve vacuum flashing, vaporization, or distillation of product from a nonvolatile catalyst composition that can result in decomposition of the phosphine ligand and precipitation of the metal component. Extractive methods of catalyst recovery, in which the catalyst components are extracted from the reaction effluent by an immiscible solvent, are known in the art but also suffer from similar disadvantages. The extracted catalyst composition typically must be concentrated by flash, vaporization or distillation away from the nonvolatile catalyst composition prior to reintroduction to the reaction zone with fresh feed substrate. These procedures often result in extended exposure of the sensitive catalyst components to damaging, elevated temperatures.

The thermal decomposition of catalyst components can be a difficult problem in the recovery of ruthenium-1,1,1-tris(diaryl- or dialkylphosphinomethyl)alkane catalysts used in hydrogenation of glycolic acid because of the high boiling points of the reaction products and complex array of reaction products and byproducts. A method for the efficient recovery of ruthenium-1,1,1-tris(diaryl- or dialkylphosphinomethyl)alkane catalyst compositions from glycolic acid hydrogenation product mixtures that reduces or avoids catalyst decomposition, therefore, would be highly desirable.

SUMMARY OF INVENTION

We have discovered that catalyst compositions comprising ruthenium and tridentate phosphorus ligands can be efficiently recovered from glycolic acid hydrogenation reaction products by an extraction process that avoids thermal or partial pressure-driven concentration methods. One aspect of our invention, therefore, is a process for recovering a homogeneous catalyst, comprising (A) extracting a glycolic acid hydrogenation product, comprising
  (i) about 10 to about 90 weight percent, ethylene glycol, based on the total weight of the glycolic acid hydrogenation product, about 1 to about 50 weight percent water, and about 0.5 to 30 weight percent of one or more reaction by-products selected from glycolic acid, oligomers of glycolic acid, and glycolate esters of ethylene glycol; and
  (ii) a catalyst composition comprising ruthenium and a tridentate ligand comprising at least one phosphine selected from 1,1,1-tris(diaryl-phosphinomethyl)alkanes and 1,1,1-tris(dialkylphosphinomethyl)alkanes;
  with a first extractant, comprising
  (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
  (ii) optionally, a hydrophilic solvent;
  to form a first raffinate phase comprising a major amount of the ethylene glycol and a minor amount of the catalyst composition contained in the glycolic acid hydrogenation product and a first extract phase comprising a major amount of the catalyst composition and a minor amount of the ethylene glycol contained in the glycolic acid hydrogenation product;

(B) separating the first raffinate and extract phases; and (C) extracting the first extract phase from step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase from step (B) and a second raffinate phase comprising a minor amount of the catalyst composition contained in the first extract phase.

The tridentate ligand can comprise a variety of 1,1,1-tris(diarylphosphino-methyl)alkanes and 1,1,1-tris(dialkylphosphinomethyl)alkanes. For example, the tridentate ligand can comprise tris-1,1,1-(diphenylphosphinomethyl)ethane. Another embodiment of the invention, therefore, is a process for recovering a homogeneous catalyst, comprising (A) extracting a glycolic acid hydrogenation product, comprising
  (i) about 40 to about 90 weight percent, ethylene glycol, based on the total weight of the glycolic acid hydrogenation product, about 0.5 to about 25 weight percent water, and about 0.5 to 30 weight percent of one or more reaction by-products selected from glycolic acid, oligomers of glycolic acid, and glycolate esters of ethylene glycol; and
  (ii) a catalyst composition comprising ruthenium and tris-1,1,1-(diphenyl-phosphinomethyl)ethane;
  with a first extractant, comprising about 60 to 100 weight percent, based on the total weight of the first extractant, 2-ethylhexanol, isobutyl isobutyrate, undecanone, methylisobutyl ketone, diisopropyl ether, or mixtures thereof, and about 0 to about 40 weight percent of a hydrocarbon having 5 to 20 carbon atoms to form a first raffinate phase comprising a major amount of the ethylene glycol and a minor amount of the catalyst composition contained in the glycolic acid hydrogenation product and a first extract phase comprising a major amount of the catalyst composition and a minor amount of the ethylene glycol contained in the glycolic acid hydrogenation product;

(B) separating the first raffinate and extract phases; and (C) extracting the first extract phase from step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase from step (B) and a second raffinate phase comprising a minor amount of the catalyst composition contained in the first extract phase.

The catalyst composition that is extracted from the first extract phase with the above second extractant can be recycled to a glycolic acid hydrogenation process without additional concentration or purification. Thus, a third aspect of our invention is a process for recovering a homogeneous catalyst, comprising (A) contacting an aqueous mixture comprising glycolic acid, glycolate esters, or mixtures thereof, with hydrogen in the presence of a catalyst composition comprising ruthenium and tris-1,1,1-(diphenylphosphinomethyl)ethane to form a glycolic acid hydrogenation product comprising about 50 to about 90 weight percent, based on the total weight of the glycolic acid hydrogenation product, ethylene glycol, about 0.5 to about 25 weight percent water, and about 0.5 to about 30 weight percent of one or more reaction by-products selected from glycolic acid, oligomers of glycolic acid, and glycolate esters of ethylene glycol, and the catalyst composition;

(B) extracting the glycolic acid hydrogenation product with a first extractant, comprising about 60 to 100 weight percent, based on the total weight of the first extractant, 2-ethylhexanol and about 0 to about 40 weight percent of a hydrocarbon having 5 to 20 carbon atoms to form a first raffinate phase comprising a major amount of the ethylene glycol contained in the glycolic acid hydrogenation product and a first extract phase comprising a major amount of the catalyst composition contained in the glycolic acid hydrogenation product;

(C) separating the first raffinate and extract phases;

(D) extracting the first extract phase from step (C) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase from step (C) and a second raffinate phase comprising a minor amount of the catalyst composition contained in the first extract phase; and (E) combining the second extract phase with the aqueous mixture of glycolic acid of step (A).

DETAILED DESCRIPTION

Figure 1:
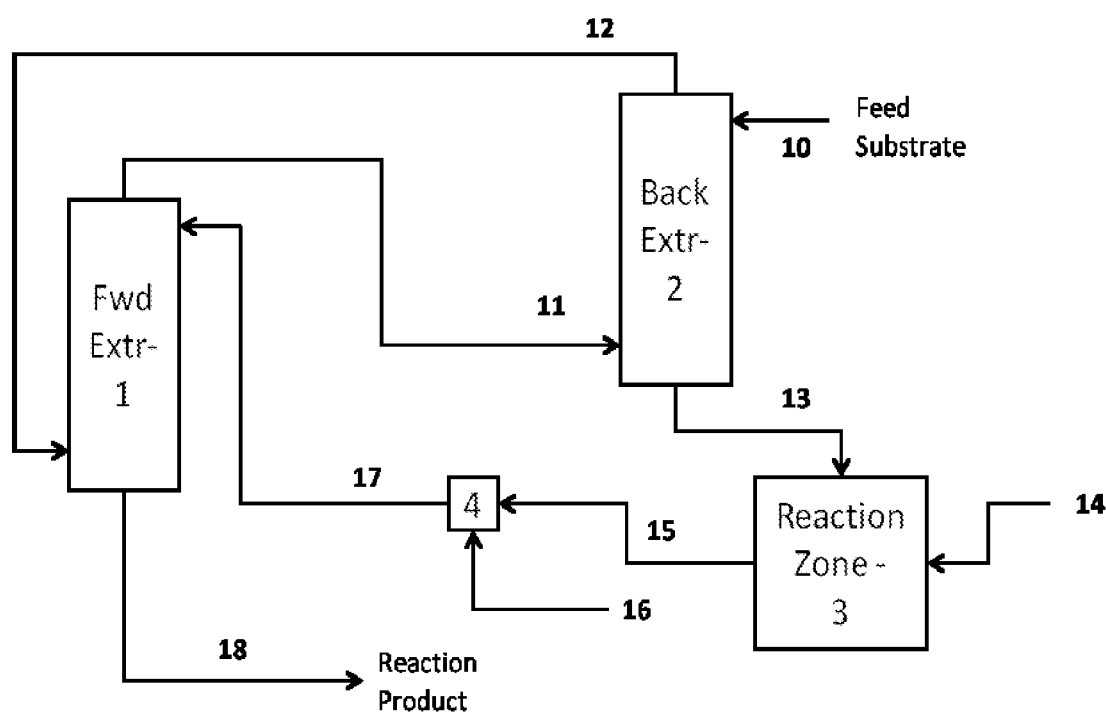
FIG. 1 is a schematic flow diagram for one embodiment of the invention in which a hydrogenated glycolic acid stream is subjected to a forward extraction with a hydrophobic solvent to produce a catalyst-rich extract that is back extracted with a hydrophilic solvent and returned to the hydrogenation reaction zone.

The present invention provides a method to recover and recycle homogeneous catalyst compositions comprising ruthenium and tridentate phosphorus ligands from glycolic acid hydrogenation products. In a general embodiment, therefore, our invention provides a process for recovering a homogeneous catalyst, comprising (A) extracting a glycolic acid hydrogenation product, comprising
  (i) about 10 to about 90 weight percent, ethylene glycol, based on the total weight of the glycolic acid hydrogenation product, about 1 to about 50 weight percent water, and about 0.5 to 30 weight percent of one or more reaction by-products selected from glycolic acid, oligomers of glycolic acid, and glycolate esters of ethylene glycol; and
  (ii) a catalyst composition comprising ruthenium and a tridentate ligand comprising at least one phosphine selected from 1,1,1-tris(diaryl-phosphinomethyl)alkanes and 1,1,1-tris(dialkylphosphinomethyl)alkanes;
  with a first extractant, comprising
  (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
  (ii) optionally, a hydrophilic solvent;
  to form a first raffinate phase comprising a major amount of the ethylene glycol and a minor amount of the catalyst composition contained in the glycolic acid hydrogenation product and a first extract phase comprising a major amount of the catalyst composition and a minor amount of the ethylene glycol contained in the glycolic acid hydrogenation product;

(B) separating the first raffinate and extract phases; and (C) extracting the first extract phase from step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase from step (B) and a second raffinate phase comprising a minor amount of the catalyst composition contained in the first extract phase.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

As used in the specification and the claims, the term "feed" is intended to have its commonly understood meaning in the liquid-liquid extraction art, that is the solution that contains the materials to be extracted or separated. In the present invention, one example of a "feed" is a reaction product or effluent from the hydrogenation of aqueous glycolic acid that typically comprises one or more of ethylene glycol, unreacted glycolic acid, mono- and diesters of glycolic acid with ethylene glycol, glycolic acid oligomers, esters of glycolic acid oligomers, other reaction byproducts, and a homogeneous catalyst composition comprising ruthenium and a tridentate phosphine ligand comprising a 1,1,1-tris(diarylphosphinomethyl)alkane or 1,1,1-tris(dialkylphosphinomethyl)alkane. Another example of a feed is a catalyst-rich hydrophobic extract from the extraction of the glycolic acid hydrogenation reaction effluent that subsequently can be extracted with a hydrophilic solvent to recover the catalyst composition in a form suitable for recycle into the hydrogenation reaction without further purification. The feed or reaction effluent also may contain various tridentate phosphine ligand degradation products formed in the reaction, and one or more solvents. The term "extraction solvent," as used herein, is intended to be synonymous with the term "extractant" or "solvent" and is intended to mean the immiscible liquid that is used in the extraction process to extract materials or solutes from the feed. In the present invention, one example of an extraction solvent is an alkanol containing 6 to 20 carbon atoms such as, for example, 2-ethylhexanol. The term "extract" is the immiscible liquid left from the extraction solvent after it has been contacted with the feed. The term "raffinate" is intended to mean the liquid phase left from the feed after it has been contacted with the extraction solvent. The term "wash solvent" is understood to mean a liquid used to wash or enhance the purity of the raffinate or extract phase.

The process of the invention provides for the recovery of a homogeneous ruthenium catalyst composition from a glycolic acid hydrogenation product. The term "glycolic acid hydrogenation product," as used herein, is understood to mean the reaction product resulting from contacting glycolic acid, one or more glycolate esters, glycolic acid oligomers, glycolate oligomer esters, or a mixture thereof with hydrogen in the presence of a homogeneous ruthenium catalyst under hydrogenation conditions of temperature and pressure to produce ethylene glycol. Similarly, the term "glycolic acid," as used herein in reference to the specification and claims, is intended to include glycolic and any glycolic acid derivatives that may be present in the reaction of formaldehyde with carbon monoxide to produce glycolic acid or in the subsequent hydrogenation of glycolic acid to produce ethylene glycol. These glycolic acid derivatives include, but are not limited to, methyl glycolate, mono- and diglycolate esters of ethylene glycol, various oligomers of glycolic acid or glycolate esters, or mixtures thereof. The term "glycolate esters," as used herein in the context of the specification and claims, is understood to mean the ester formed between glycolic acid or one or more oligomers of glycolic acid and an alcohol, a diol, or a polyol. Examples of glycolate esters are the glycolate esters of ethylene glycol, which can be a monoester of ethylene glycol and glycolic acid or a glycolic acid oligomer, a diester of ethylene glycol and glycolic acid or a glycolic acid oligomer, or a mixture of mono- and diesters of ethylene glycol and glycolic acid or a glycolic acid oligomer. The term "glycolic acid oligomer" is intended to have its commonly understood meaning in the art, that is a dimer, trimer, or low molecular weight polymer of glycolic acid or a glycolic acid ester typically having 2 to about 20 repeating units. More typically, the glycolic acid oligomers can have 2 to about 6 repeating units. The glycolic acid may be obtained from any source known in the art such as, for example, from commercial sources. Our invention is illustrated, however, with particular reference to glycolic acid mixtures prepared by contacting aqueous solutions of formaldehyde with carbon monoxide in the presence of an acid catalyst under elevated pressures and temperatures. These reactions are referred to herein as the "hydrocarboxylation" of formaldehyde and are exemplified in U.S. Pat. Nos. 2,152,852; 2,153,064; 2,211,624; 2,211,625; and 3,948,977; and United Kingdom Patent No. 1,499,245.

The glycolic hydrogenation product of the present invention can be produced by contacting glycolic acid, as defined above, with hydrogen at elevated pressures and temperatures in the presence of the homogeneous ruthenium catalyst compositions described herein. Thus, for example, ethylene glycol can be produced from glycolic acid, glycolate esters, oligomers of glycolic acid, esters of glycolic acid oligomers, or mixtures thereof. The term "homogeneous" means any ruthenium compound such as, for example, a ruthenium-phosphine coordination compound that is soluble or partly soluble in the reaction mixture. Similar processes have been described in the art such as, for example, as disclosed in U.S. Pat. No. 7,615,671. In addition to unreacted glycolic acid and hydrogenation catalyst components, the glycolic acid hydrogenation reaction product typically can comprise mono- and bis-glycolate esters of ethylene glycol, glycolic acid, oligomers of glycolic acid typically having 2 to 6 glycolic acid repeating units, bis- and mono-esters of ethylene glycol and glycolic acid oligomers typically having two to six glycolic acid units, water, and ethylene glycol.

The hydrogenation reaction may be conducted under moderate conditions using a variety of procedures known in the art. Typically, the hydrogen pressure over the reaction mixture can be about 3.5 to about 27 megapascals (MPa). Lower pressures will generally result in a slower rate of reaction. Higher pressures give a faster rate of reaction, but this is offset by higher operating costs. A typical temperature range for the hydrogenation reaction is about 150 to about 220° C. For example, the hydrogenation of glycolic acid can be carried out at a temperature of about 180 to about 210° C. and a pressure of about 6 to about 16 MPa. The hydrogen feed can comprise at least 95 mole % hydrogen or, in another example, greater than 99 mole % hydrogen.

The glycolic acid hydrogenation reaction is conducted for a period of time sufficient to produce the desired products while minimizing unwanted by-products. Persons having ordinary skill in the art will understand that reaction time will be dependent, in part, upon factors such as temperature, pressure, catalyst concentration, nature and proportion of starting materials, and the like. The reaction time will typically be within the range of from about one-half to about 200 hours or more. For example, the reaction time can be from less than about one to about 10 hours.

The hydrogenation of glycolic acid and the resulting glycolic acid hydrogenation product may comprise a solvent. The solvent can be water or a hydrophilic organic solvent. The term "hydrophilic," as used herein, is understood to mean that equal volumes of the solvent and water are completely miscible at the temperature of the reaction or extraction processes described herein. Similarly, the term "hydrophobic," is understood to mean that equal volumes of the solvent and water are immiscible or partially miscible at the reaction or extraction temperature described herein. The solvent should dissolve the catalyst components and reactants, and should not act as a poison to the catalyst. Examples of hydrophilic organic solvents include lower alcohols, glycolic acid hydrogenation reaction starting materials, and glycolic acid hydrogenation reaction products. Some specific examples of hydrophilic organic solvents include methanol, ethanol, propanol, isopropanol, ethylene glycol, glycolic acid, glycolate esters, oligomers of glycolic acid and glycolate esters, 1,2-propylene glycol, 1,3-propylene glycol, 2-methyl-1,3-propanediol, neopentyl glycol, 2-ethylhexanol, 1,4-butanediol, diethylene glycol, triethylene glycol, glycerol, methoxy ethanol, and mixtures thereof.

Any of the known hydrogenation reactor designs or configurations may be used for the hydrogenation reaction to produce the glycolic acid hydrogenation product. For example, the process may be conducted in a batchwise manner in an autoclave by contacting the glycolic acid with hydrogen in the presence of the catalyst compositions described herein. It will be apparent to those skilled in the art that other reactor schemes may be used with this invention. For example, the hydrogenation reaction can be conducted in a plurality of reaction zones, in series, in parallel, or it may be conducted batchwise or continuously in a tubular plug flow reaction zone or series of such zones with recycle of unconsumed feed substrate materials if required. The reaction steps may be carried out by the incremental addition of one of the feed substrate materials to the other. Also, the reaction steps can be combined by the joint addition of the feed substrate materials.

The glycolic acid hydrogenation process and products thereof comprise a catalyst composition comprising ruthenium and a tridentate ligand comprising at least one phosphine selected from 1,1,1-tris(diarylphosphinomethyl)alkanes and 1,1,1-tris(dialkylphosphinomethyl)alkanes. The source of ruthenium is not particularly limiting and can be any ruthenium compound that is soluble in the hydrogenation reaction medium. Some non-limiting examples of ruthenium compounds include ruthenium salts, hydride complexes, carbonyl compounds, halides, oxides, phosphine complexes, and mixtures thereof. Suitable ruthenium salts include ruthenium carboxylates and acetylacetonates. For example, the ruthenium compound can comprise the acetonylacetonate or diacetate salts of a ruthenium coordination compound with any of the tridentate ligands set forth herein.

The tridentate ligand can comprise at least one phosphine selected from 1,1,1-tris(diarylphosphinomethyl)alkanes and 1,1,1-tris(dialkylphosphinomethyl)alkanes having the formula (I):

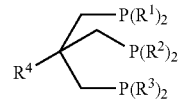

I wherein $R^4$ represents a substituted or unsubstituted, straight or branched chain alkyl radical having 1 to 40 carbon atoms or a substituted or unsubstituted cycloaliphatic radical containing 6 to 40 carbon atoms; and $R^1$, $R^2$, $R^3$ each independently may be a substituted or unsubstituted alkyl radical having 1 to 40 carbon atoms, an substituted or unsubstituted aryl radical having 6 to 20 carbon atoms, or a substituted or unsubstituted cycloaliphatic radical have 6 to 20 carbon atoms.

The alkyl radicals represented by $R^1$, $R^2$, $R^3$, and $R^4$ can be substituted with any group that does not interfere with the hydrogenation reaction such as, for example, hydroxyl, ether, halogen, sulfonic acid, carboxylic acid, and the like. Examples of substituted and unsubstituted alkyl radicals include, but are not limited to, methyl, ethyl, cyanomethyl, nitromethyl, hydroxymethyl, trityloxymethyl, propionyloxymethyl, aminomethyl, carboxymethyl, methoxymethyl, ethoxymethyl, butoxymethyl, t-butoxymethyl, acetoxymethyl, chloromethyl, bromomethyl, iodomethyl, 6-hydroxyhexyl, 2,4-dichloro(n-butyl), 2-amino(isopropyl), n-propyl, isopropyl, isobutyl, n-butyl, tertiary butyl, pentyl, hexyl, 2-ethylhexyl, octyl, decyl, and various isomers thereof.

Examples of substituted and unsubstituted cycloalkyl radicals include, but are not limited to, cyclopropyl, cyclobutyl, hydroxymethylcyclobutyl, cyclopentyl, cyclohexyl, cycloheptyl, 2-methylcyclopropyl, 4-methylcyclohexyl, 4-(isopropyl)-cyclohexylethyl or 2-methyl-cyclopropylpentyl, and the like. Examples of substituted and unsubstituted aryl radicals are phenyl, napthyl, anthracenyl, 4-chlorophenyl, 2,6-dichlorophenyl, 2,5-dichlorophenyl, 3,4-dichlorophenyl, 3-chlorophenyl, 3-bromophenyl, 4-bromo-indenyl, 3,4-dibromophenyl, 3,4-dibromonaphthyl, 3-chloro-4-fluorophenyl, 2-fluoro-phenyl, 4-hydroxyphenyl, 3-hydroxyphenyl, 2,4-dihydroxyphenyl, 4-cyanophenyl; 4-methylphenyl, 2,4-dimethylphenyl, 2-methylnaphthyl, 4-(isopropyl)phenyl, 4-ethyl-naphthyl, 3-(n-propyl)phenyl, 2,6-dimethoxyphenyl, 4-methoxyphenyl, 3-ethoxyindenyl, 4-(iso-propoxy)phenyl, 4-(t-butoxy)phenyl, 3-ethoxy-4-methoxyphenyl, 3- or 4-trifluoro-methylphenyl, 3,4-di(hydroxymethyl)phenyl, 2-(aminomethyl)phenyl, and 3-(methyl-sulfonylamino)naphthyl.

Exemplary tridentate phosphine ligands include, but are not limited to, tris-1,1,1-(diphenylphosphinomethyl)methane, tris-1,1,1-(diphenylphosphinomethyl)ethane, (2-(butoxymethyl)-2-((diphenylphosphino)methyl)propane-1,3-diyl)bis(di-phenylphosphine), (2-(benzyloxymethyl)-2-((diphenylphosphino)methyl)propane-1,3-diyl)bis (diphenylphosphine), tris-1,1,1-(diphenylphosphinomethyl) propane, tris-1,1,1-(diphenylphosphino-methyl)butane, tris-1,1,1-(diphenylphosphinomethyl)-2,2-dimethylpropane, tris-1,1,1-(diphenylphosphinomethyl)cyclohexane, tris-1,1,1-(dicyclohexylphosphinomethyl)ethane, tris-1,1,1-(dimethylphosphinomethyl)ethane, tris-1,1,1-(diethylphosphinomethyl)ethane, or mixtures thereof. For example, the tridentate phosphine can comprise 1,1,1-tris(diphenylphosphinomethyl)ethane (also known as "triphos"), represented by formula (II), 1,1,1-tris(diethylphosphino-methyl)ethane, represented by formula (III), (2-(butoxymethyl)-2-((diphenylphosphino)-methyl)propane-1,3-diyl)bis(diphenylphosphine), represented by formula (IV), (2-(benzyloxymethyl)-2-((diphenylphosphino)methyl)propane-1,3-diyl)bis(diphenyl-phosphine), represented by formula (V), or a poly(alkylenoxymethyl)-2-((diphenylphosphino)methyl)propane-1,3-diyl)bis(diphenylphosphine), represented by formula (VI):

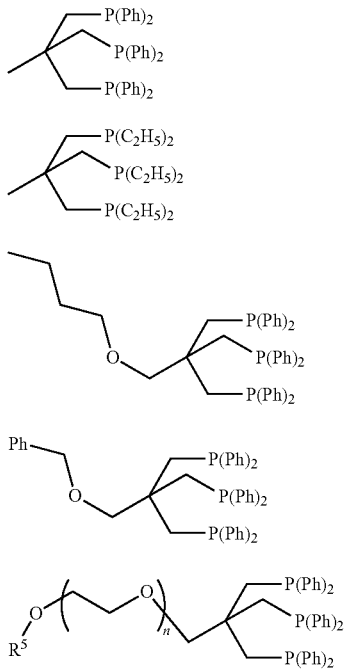

wherein n is 1 to 10 and $R^5$ is an alkyl or substituted alkyl group having 1 to 20 carbon atoms.

The phosphorus ligands represented by formulas (IV), (V), and (VI) can show higher solubility in the extraction solvents disclosed herein for the process of the invention in comparison to ligands (II) and (III). These ligands can be readily prepared, as shown in FIG. 5, by the reaction of pentaerythritol (VII) with thionyl chloride in presence of pyridine to produce pentaerythrityl tetrachloride (IX) and pentaerythrityl trichlorohydrin (VIII) as disclosed in Mondanaro, K.; Lynch, M.; Dailey, W. *J. Org. Chem.*, 1995, 60, 4666-4668. Compound (VIII) can be reacted with n-butyl bromide in presence of potassium hydroxide (KOH) at low temperature to give 1-(3-Chloro-2,2-bis(chloromethyl)propoxy)butane (X). Compound (X) can then be reacted with 3 equivilants of lithium diphenylphosphide (LiPPh₂) in diethoxy methane solvent to form (IV). Persons skilled in the art will recognize that similar steps may be used to prepare compounds (V) and (VI).

FIG. 5

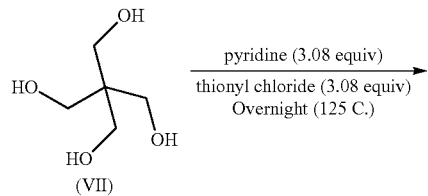

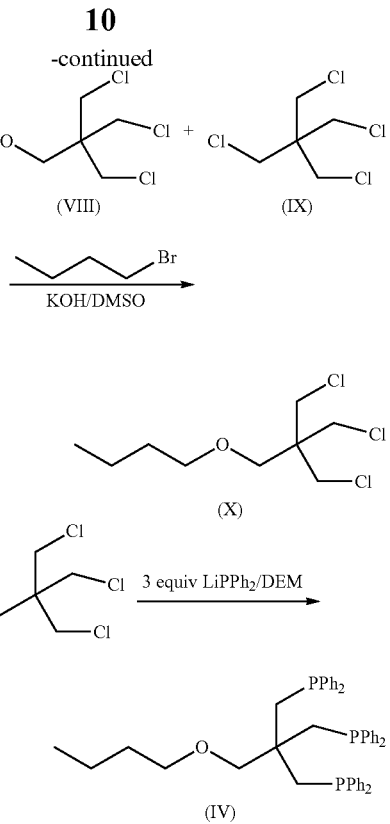

Compounds (IV), (V), and (VI) can be purified by reaction with a limiting amount of tris(triphenylphosphine)ruthenium dichloride((Ph₃P)₃RuCl₂) in toluene to produce Cl-bridged complexes of these compounds. These bridged complexes can be isolated by crystallization in high purity and yield.

The concentration of the ruthenium and the tridentate ligand in the glycolic acid hydrogenation reaction mixture or product can vary over a wide range. In general, Ru concentrations (as the free metal) can be in the range of from about 1 part per million to about 10,000 parts per million. For example, Ru concentrations in the range of from about 10 part per million to about 1,000 parts per million can be used. In another example, the Ru concentration can be 20 part per million to about 200 parts per million. Typically, a gram mole ligand:gram atom ruthenium ratio of at least 1:1 is maintained in the reaction mixture. More typically, the ratio ranges from 1:1 to 20:1 or 3:1 to 5:1.

Our process comprises extracting a glycolic acid hydrogenation product that comprises about 10 to about 90 weight percent, ethylene glycol, based on the total weight of the glycolic acid hydrogenation product, about 1 to about 50 weight percent water, and about 0.5 to 30 weight percent of one or more reaction by-products selected from glycolic acid, oligomers of glycolic acid, and glycolate esters of ethylene glycol. In addition, the glycolic acid hydrogenation product comprises a catalyst composition comprising ruthenium and a tridentate ligand comprising at least one phosphine selected from 1,1,1-tris(diarylphosphinomethyl)alkanes and 1,1,1-tris(dialkyl-phosphinomethyl)alkanes. In another example, the glycolic acid hydrogenation product can comprise about 40 to about 90 weight percent ethylene glycol about 0.5 to about 25 weight percent water, and about 0.5 to 15 weight percent of the one or more reaction by-products noted above. In yet another example, the glycolic acid hydrogenation product can comprise about 50 to about 90 weight percent, based on the total weight of the glycolic acid hydrogenation product, ethylene glycol, about 0.5 to about 25 weight percent water, and about 0.5 to about 30 weight percent of one or more reaction by-products described above, and the above catalyst composition.

As described previously, the catalyst composition comprises ruthenium and a tridentate ligand comprising at least one phosphine selected from 1,1,1-tris(diaryl-phosphinomethyl)alkanes and 1,1,1-tris(dialkylphosphinomethyl)alkanes. Some non-limiting examples of 1,1,1-tris(diarylphosphinomethyl)alkanes and 1,1,1-tris(dialkylphosphinomethyl)alkanes include 1,1,1-(diphenylphosphinomethyl)methane, tris-1,1,1-(diphenylphosphinomethyl)ethane, (2-(butoxymethyl)-2-((diphenylphosphino)-methyl)propane-1,3-diyl)bis (diphenylphosphine), (2-(benzyloxymethyl)-2-((diphenylphosphino)methyl)propane-1,3-diyl)bis (diphenylphosphine), tris-1,1,1-(diphenylphosphinomethyl)propane, tris-1,1,1-(diphenylphosphinomethyl)butane, tris-1,1,1-(diphenylphosphinomethyl)-2,2-dimethylpropane, tris-1,1,1-(diphenylphosphino-methyl)cyclohexane, tris-1,1,1-(dicyclohexylphosphinomethyl)ethane, tris-1,1,1-(dimethylphosphinomethyl)ethane, tris-1,1,1-(diethylphosphinomethyl)ethane, or mixtures thereof. For example, the catalyst composition can comprise a tridentate ligand comprising 1,1,1-(diphenylphosphinomethyl)ethane, (2-(butoxymethyl)-2-((diphenylphosphino)methyl)propane-1,3-diyl)bis(diphenylphosphine), (2-(benzyloxymethyl)-2-((diphenylphosphino)methyl)propane-1,3-diyl)bis(di-phenylphosphine), or mixtures thereof. In another embodiment, the tridentate ligand can comprise 1,1,1-(diphenylphosphinomethyl)ethane.

The glycolic acid hydrogenation product is contacted with a first extractant that comprises at least one hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof. Some representative examples of hydrophobic solvents include, but are not limited to, 2-ethylhexanol, n-heptanol, n-hexanol, n-octanol, n-nonanol, n-decanol, tetradecanol isomers, methyl isobutylketone, methyl isopropylketone, isobutylisobutyrate, ethyl acetate, n-butyl acetate, isobutylacetate, isopropylacetate, n-propyl acetate, diisopropylether, dibutylether, tertiary-amyl methyl ether, 2-ethylhexanoic acid, and mixtures thereof. For example, in one embodiment of our inventive process, the hydrophobic extraction solvent comprises 2-ethylhexanol.

Mixtures of one or more different hydrophobic solvents may be employed if desired. The amount of hydrophobic extraction solvent employed is not critical to the subject invention and need only be that amount sufficient to extract the one or more products from the reaction effluent for any given process and to ensure the formation of two immiscible liquid phases throughout the extraction zones. In general, the amount of hydrophobic extraction solvent employed may range from about 5 percent by weight up to about 500 percent by weight or more based on the total weight of the reaction product fluid. The use of the high percentage of hydrophobic extraction solvent may be necessary, for example, when there are only a limited number of stages in a countercurrent extraction process.

The hydrophobic solvent of the first extractant may further comprise a hydrocarbon to modify the physical and transport properties of the extractant. The hydrocarbon can have from 4 to 20 carbon atoms. Some representative examples of hydrocarbons include hexane, heptane, octane, decane, benzene, toluene, xylenes, methyl napththalenes, and mixtures thereof. For example, the hydrocarbon may comprise isoparaffinic mixed hydrocarbons having boiling ranges between about 90 and about 325° C., as exemplified by the ISOPAR™ solvents, such as ISOPAR C (boiling point range of 98 to 104° C.), Isopar E (boiling point range of 118 to 137° C.), ISOPAR G (boiling point range of 160 to 176° C.), ISOPAR H (boiling point range of 178 to 188° C.), ISOPAR K (boiling point range of 178 to 197° C.), ISOPAR L (boiling point range of 189 to 207° C.), ISOPAR C (boiling point range of 223 to 254° C.), and ISOPAR V (boiling point range of 273 to 312° C.).

In some aspects of the invention, the hydrocarbon can be lower boiling than the other hydrophobic solvent components and, thus, can be readily separated from the other components by distillation. If more than one hydrophobic solvent is used as the first extractant, these solvents may or may not form azeotropic mixtures under distillation conditions employed.

The first extractant may optionally comprise a hydrophilic solvent selected from water, nitriles having from 2 to 3 carbon atoms, alkoxynitriles having from 4 to 6 carbon atoms, alkanols having from 1 to 3 carbon atoms, alkoxyalcohols having from 2 to 6 carbon atoms, pyrrolidones having from 4 to 6 carbon atoms, formamides having from 4 to 6 carbon atoms, sulfoxides having from 4 to 6 carbon atoms, diols having from 2 to 6 carbon atoms, polyols having 2 to 6 carbon atoms, acetic acid, formic acid, α-hydroxy carboxylic acids having from 4 to 6 carbon atoms, glycolic acid oligomers having 2 to 6 repeat units, glycolate esters, and mixtures thereof. For purposes of this invention, one or more glycolic acid hydrogenation product or reactants may be used as the hydrophilic solvent. In general, the amount of hydrophilic solvent employed may range from about 1 weight percent, based on the total weight of the extractant, to about 60 weight percent. Some additional weight percent ranges of the hydrophilic solvent are about 1 to about 50 weight percent and about 1 to about 40 weight percent.

As noted above, the optional, hydrophilic solvent used in the first extractant can be a hydrophilic component present in the glycolic acid hydrogenation product. For example, in the hydrogenation of glycolate esters to produce ethylene glycol, the optional, hydrophilic extraction solvent can comprise ethylene glycol. In another example, the hydrophilic solvent can comprise one or more glycolate esters as described hereinabove. The optional hydrophilic solvent can be introduced to the extraction process at one or more different locations. In one embodiment for example, the optional hydrophilic solvent can be added to the first extractant. In another embodiment, the hydrophilic solvent can be added to the first extractant directly, to the glycolic acid hydrogenation product, or to the extractor containing a mixture of the extractant and glycolic acid hydrogenation product. In another embodiment, the hydrophilic solvent can be introduced into the extractor as a separate feed. In yet another embodiment, the extractor may be operated as a fractional extractor with one or more hydrophilic extraction solvent feed points. In still another embodiment, for example, the hydrophilic extraction solvent for the forward extraction zone can be water. In still another embodiment, sufficient water can be added to the extractor to produce a water content in the a first raffinate phase exiting the forward extraction zone of about 0 to 60 weight percent water or, in another example about 5 to 35 weight percent water, based on the total weight of the first raffinate phase.

The ratio of the hydrophilic and hydrophobic solvents used in the process of the invention can depend on the composition of the glycolic acid hydrogenation product. For example, as the concentration of the hydrophilic or hydrophobic solvents in the glycolic acid hydrogenation reaction effluent becomes lower, it may be required to increase the ratio of the hydrophobic extraction solvent to the glycolic acid hydrogenation reaction product fluid, the ratio of the hydrophilic extraction solvent to the reaction product fluid, or both. Generally, the volume ratio of either the hydrophilic or hydrophobic extraction solvent to the reaction effluent may be changed within a range of from about 20:1 to about 1:20.

The extraction of the glycolic acid hydrogenation product can be carried out by any means known in the art to intimately contact two immiscible liquid phases and to separate the resulting phases after the extraction procedure. For example, the extraction can be carried out using columns, centrifuges, mixer-settlers, and miscellaneous devices. Some representative examples of extractors include unagitated columns (e.g., spray, baffle tray and packed, perforated plate), agitated columns (e.g., pulsed, rotary agitated, and reciprocating plate), mixer-settlers (e.g., pump-settler, static mixer-settler, and agitated mixer-settler), centrifugal extractors (e.g., those produced by Robatel, Luwesta, deLaval, Dorr Oliver, Bird, CINC, and Podbielniak), and other miscellaneous extractors (e.g., emulsion phase contactor, electrically enhanced extractors, and membrane extractors). A description of these devices can be found in the "Handbook of Solvent Extraction", Krieger Publishing Company, Malabar, Fla., 1991, pp. 275-501. The various types of extractors may be used alone or in any combination.

The extraction may be conducted in one or more stages. The number of extraction stages can be selected in consideration of capital costs, achieving high extraction efficiency, ease of operability, and the stability of the starting materials and reaction product to the extraction conditions. The extraction also can be conducted in a batch or continuous fashion. In a continuous mode, the extraction may be carried out in a co-current, a counter-current manner, or as a fractional extraction in which multiple solvents and/or solvent feed points are used to help facilitate the separation. The extraction process also can be conducted in a plurality of separation zones that can be in series or in parallel.

The extraction typically can be carried out at a temperature of about 10 to about 120° C. For example, the extraction can be conducted at a temperature of about 30 to about 80° C. The desired temperature range may be constrained further by the boiling point of the extractant components. Generally, it is undesirable to operate the extraction under conditions where the extractant boils. In one embodiment, the extractor can be operated to establish a temperature gradient across the extractor in order to improve the mass transfer kinetics or decantation rates.

The glycolic acid hydrogenation product and extractant can be contacted by fractional extraction methods such as, for example, by fractional countercurrent extraction. As used herein, the term "fractional countercurrent extraction" is intended to include, but is not limited to, a method for separating a feed stream, e.g., reaction product fluid, containing two or more substances by charging the feed stream to a countercurrent extraction process between the points where two immiscible solvents are charged to the extraction process. The two immiscible solvents should be immiscible over the entire temperature range of the extraction process. This method is sometimes referred to as "double solvent extraction." Fractional countercurrent extraction can involve the use of a cascade of stages, extracting solvents and solution to be extracted entering at opposite ends of the cascade with the feed phase and hydrophobic extractant phase flowing countercurrently. Some example fractional countercurrent extraction configurations may be found in Treybal, *Liquid Extraction*, 2nd Edition, McGraw-Hill Book Company, New York. 1963, pp. 275-276.

When conducted in a fractional extraction mode, the hydrophobic extraction solvent typically can be added to the extraction zone at a point closer to the end of the extractor where the first raffinate phase exits the extraction zone and further away from the optional hydrophilic extraction solvent feed point. The mass feed ratio of the hydrophilic solvent contained in the reactor effluent and the hydrophilic extraction solvent added directly to the forward extraction zone typically can be between about 0 and 1.5. In another example, The mass feed ratio can be between about 0.05 to 0.45.

The extraction of the glycolic acid hydrogenation product produces a first raffinate phase comprising a major amount of the ethylene glycol contained in the glycolic acid hydrogenation product and a first extract phase comprising a major amount of the catalyst composition in the glycolic acid hydrogenation product. The first raffinate phase and the first extract phase may be separated by any phase separation technology known in the art. The phase separation techniques can be accomplished in the extractor or in a separate liquid-liquid separation device. Suitable liquid-liquid separation devices include, but are not limited to, coalescers, cyclones and centrifuges. Typical equipment that can be used for liquid-liquid phase separation devices are described in the *Handbook of Separation process Technology*, ISBN 0-471-89558-X, John Wiley & Sons, Inc., 1987.

The catalyst composition can be back-extracted from the first extract phase into a hydrophilic solvent that subsequently can be used directly as a reactant in the glycolic acid hydrogenation reaction. Thus, our process also comprises extracting the first extract phase from step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase from step (B) and a second raffinate phase comprising a minor amount of the catalyst composition contained in the first extract phase. Typically, the concentration of Ru in the second extract phase can be about 10 parts per million to about 10,000 parts per million or, in another example, about 20 part per million to about 200 parts per million, and recycled to the glycolic acid hydrogenation reaction without further concentration of the catalyst.

The second extract phase can be passed to a process for the preparation of ethylene glycol by hydrogenation of glycolic acid, glycolate esters, glycolic acid oligomers, or mixtures thereof. The second raffinate phase can be recycled to the first extraction by combining the second raffinate phase with the first extractant. The second raffinate phase can be distilled prior to recycle to produce a hydrophobic solvent distillate that is subsequently combined with the extractant of step (A). Thus, in another embodiment, the process of the invention can further comprise combining the second raffinate phase of step (C) with the first extractant of step (A), or distilling the second raffinate phase of step (C) to produce a hydrophobic solvent distillate and combining the hydrophobic solvent distillate with the first extractant of step (A).

The weight ratio of the second extractant to the first extract phase from step (B) of our inventive process about 0.05:1 to about 2:1. Further examples of weight ratios of the second extractant to the first extract phase are about 0.1:1 to 2:1 and about 0.1:1 to about 1:1.

The extraction process can be conducted at a temperature of about 10 to about 120° C. For example, in one embodiment of the invention, steps (A)-(C) of the invention are carried out at a temperature of about 30 to about 80° C.

In another embodiment of our process, the second extractant can comprise mono- and diglycolate esters of ethylene glycol. In another example, the catalyst composition can comprise tris-1,1,1-(diphenylphosphinomethyl)ethane, the first extractant can comprise a hydrophobic solvent comprising 2-ethylhexanol and heptane, and the second extractant can comprise mono- and diglycolate esters of ethylene glycol. The extraction step (C) also can be carried out by any extraction means known in the art such, for example, by fractional extraction methods. For example, steps (A), (C), or (A) and (C) of the process of the invention can be carried out by fractional countercurrent extraction.

Another aspect of our invention is process for recovering a homogeneous catalyst, comprising (A) extracting a glycolic acid hydrogenation product, comprising
  (i) about 40 to about 90 weight percent, ethylene glycol, based on the total weight of the glycolic acid hydrogenation product, about 0.5 to about 25 weight percent water, and about 0.5 to 30 weight percent of one or more reaction by-products selected from glycolic acid, oligomers of glycolic acid, and glycolate esters of ethylene glycol; and
  (ii) a catalyst composition comprising ruthenium and tris-1,1,1-(diphenyl-phosphinomethyl)ethane;
  with a first extractant, comprising about 60 to 100 weight percent, based on the total weight of the first extractant, 2-ethylhexanol, isobutyl isobutyrate, undecanone, methylisobutyl ketone, diisopropyl ether, or mixtures thereof, and about 0 to about 40 weight percent of a hydrocarbon having 5 to 20 carbon atoms to form a first raffinate phase comprising a major amount of the ethylene glycol and a minor amount of the catalyst composition contained in the glycolic acid hydrogenation product and a first extract phase comprising a major amount of the catalyst composition and a minor amount of the ethylene glycol contained in the glycolic acid hydrogenation product;
(B) separating the first raffinate and extract phases; and
(C) extracting the first extract phase from step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase from step (B) and a second raffinate phase comprising a minor amount of the catalyst composition contained in the first extract phase.

It is understood that the above process comprises the various embodiments of the glycolic acid hydrogenation product, the catalyst composition, the first extractant, the second extractant, equipment used to carry out the extractions, and the first and second extract phases steps as described previously. For example, the glycolic acid hydrogenation product can comprise about 40 to about 90 weight percent ethylene glycol about 0.5 to about 25 weight percent water, and about 0.5 to 15 weight percent of the one or more reaction by-products noted above. In another example, the glycolic acid hydrogenation product can comprise about 50 to about 90 weight percent, based on the total weight of the glycolic acid hydrogenation product, ethylene glycol, about 0.5 to about 25 weight percent water, and about 0.5 to about 30 weight percent of one or more reaction by-products described above, and the above catalyst composition.

The first extractant comprises about 60 to 100 weight percent, based on the total weight of the first extractant, 2-ethylhexanol, isobutyl isobutyrate, undecanone, methylisobutyl ketone, diisopropyl ether, or mixtures thereof, and about 0 to about 40 weight percent of a hydrocarbon having 5 to 20 carbon atoms. Some representative examples of hydrocarbons include hexane, heptane, octane, decane, benzene, toluene, xylenes, methyl napththalenes, and mixtures thereof. For example, the hydrophobic solvent can comprise 2-ethylhexanol and heptane.

As noted previously, the extraction of the glycolic acid hydrogenation product can be carried out by any means known in the art to intimately contact two immiscible liquid phases and to separate the resulting phases after the extraction procedure. For example, the extraction can be carried out using columns, centrifuges, mixer-settlers, and miscellaneous devices. The various types of extractors may be used alone or in any combination.

The extraction may be conducted in one or more stages. The extraction also can be conducted in a batch or continuous fashion. In a continuous mode, the extraction may be carried out in a co-current, a counter-current manner, or as a fractional extraction in which multiple solvents and/or solvent feed points are used to help facilitate the separation. Further, the extraction process of this invention can be conducted in a plurality of separation zones in series or in parallel. The extraction typically can be carried out at a temperature of about 10 to about 120° C. The glycolic acid hydrogenation product and extractant can be contacted by fractional extraction methods such as, for example, by fractional countercurrent extraction as described above.

The extraction produces a first raffinate phase comprising a major amount of the ethylene glycol contained in the glycolic acid hydrogenation product and a first extract phase comprising a major amount of the catalyst composition in the glycolic acid hydrogenation product. The raffinate and extract phases may be separated by any phase separation technology known in the art as described hereinabove.

The catalyst composition can be back-extracted from the first extract phase into a solvent mixture that subsequently can be used directly as a reactant in the glycolic acid hydrogenation reaction. Thus, our process also comprises extracting the first extract phase from step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase from step (B) and a second raffinate phase comprising a minor amount of the catalyst composition contained in the first extract phase.

The second extract phase can be passed to a process for the preparation of ethylene glycol by hydrogenation of glycolic acid, glycolate esters, glycolic acid oligomers, or mixtures thereof. The second raffinate phase can be recycled to the first extraction by combining the second raffinate phase with the first extractant. The second raffinate phase can be distilled prior to recycle to produce a hydrophobic solvent distillate that is subsequently combined with the extractant of step (A). Thus, in another embodiment, the process of the invention can further comprise combining the second raffinate phase of step (C) with the first extractant of step (A), or distilling the second raffinate phase of step (C) to produce a hydrophobic solvent distillate and combining the hydrophobic solvent distillate with the first extractant of step (A).

In one embodiment of our process, the glycolic acid hydrogenation reactor effluent comprises ethylene glycol, ruthenium and at least one phosphine selected from 1,1,1-tris(diarylphosphinomethyl)alkanes and 1,1,1-tris(dialkylphosphinomethyl)alkanes, water, and some byproducts. The reactor effluent is fed to the forward extraction zone, wherein the reactor effluent is contacted in a countercurrent extraction column with a hydrophobic solvent extractant. The hydrophobic solvent comprises an alkanol, having 6 to 14 carbon atoms, and a hydrocarbon solvent. Water is optionally added to the forward extractor as the hydrophilic solvent as necessary to improve the extractor performance based on physical and transport properties as well as the equilibrium. The hydrophilic raffinate phase comprises a majority of the ethylene glycol. The hydrophobic solvent to feed ratio and staging is adjusted such that the amount of phosphine-Ru catalyst composition lost with the hydrophilic raffinate phase is economically acceptable and does not require a subsequent recovery step. The hydrophobic extract phase may be then fed to a back extraction zone, wherein the hydrophobic extract phase can be contacted in a countercurrent extraction column with a hydrophilic extractant, comprising the feed substrate to the reaction zone, i.e., glycolic acid, mono and bis glycolates of ethylene glycol, oligomers of glycolic acid, and the like. An additional second hydrophobic solvent optionally can be added to the back extractor as necessary to improve the extractor performance. This second hydrophobic solvent may comprise a hydrocarbon having 4 to 20 carbon atoms such as, for example, hexane, heptane, octane, decane, benzene, toluene, xylenes, methyl napththalenes, or mixtures thereof. The second hydrophobic solvent to feed ratio and staging is adjusted such that the amount of phosphine-Ru catalyst complex lost with the second raffinate phase is economically acceptable and does not require a subsequent recovery step. The second extract phase from the back extraction zone is suitable to charge to the hydrogenation reactor directly after it exits the back extraction zone. The second raffinate phase is suitable for recycle to the forward extraction zone as the hydrophobic solvent. Optionally, the second hydrophobic solvent added to the back extraction zone is produced, for example by distillation, from the second raffinate phase before it is recycled to the forward extraction zone.

Optionally, an additional hydrophobic solvent may be employed to modify the physical and transport properties of the hydrophobic extractant mixture prior to introduction into the back extraction zone. This additional hydrophobic solvent can be the same as the optional, second hydrophobic solvent employed in the forward extraction zone. The optional addition of the second hydrophobic extraction solvent can be used to remove any unwanted relatively hydrophobic components from the hydrophilic extraction phase of the back extractor zone. In one embodiment, the second hydrophobic extraction solvent is not required, and the second extractor is operated as a traditional extractor instead of as a fractional extractor.

Alternatively, the back extraction zone may be operated in a fractional extraction mode with the additional second hydrophobic solvent added at a feed point closer to the end of the extractor where the raffinate stream exits than the feed point of the hydrophobic extract phase from the forward extraction zone. Preferably the mass feed ratio of the additional second hydrophobic solvent to the hydrophobic extract phase from the forward extraction zone is between 0 and 1.5, more preferably about 0.05 to 0.45.

As noted above, the process of the invention can comprise recycling the recovered catalyst composition to a process for the preparation of ethylene glycol by hydrogenation of glycolic acid, glycolate esters, glycolic acid oligomers, or mixtures thereof. Thus, another embodiment of the invention is a process for recovering a homogeneous catalyst, comprising (A) contacting an aqueous mixture comprising glycolic acid, glycolate esters, oligomers of glycolic acid, or mixtures thereof, with hydrogen in the presence of a catalyst composition comprising ruthenium and tris-1,1,1-(diphenylphosphinomethyl)ethane to form a glycolic acid hydrogenation product comprising about 50 to about 90 weight percent, based on the total weight of the glycolic acid hydrogenation product, ethylene glycol, about 0.5 to about 25 weight percent water, and about 0.5 to about 30 weight percent of one or more reaction by-products selected from glycolic acid, oligomers of glycolic acid, and glycolate esters of ethylene glycol, and the catalyst composition;

(B) extracting the glycolic acid hydrogenation product with a first extractant, comprising about 60 to 100 weight percent, based on the total weight of the first extractant, 2-ethylhexanol and about 0 to about 40 weight percent of a hydrocarbon having 5 to 20 carbon atoms to form a first raffinate phase comprising a major amount of the ethylene glycol contained in the glycolic acid hydrogenation product and a first extract phase comprising a major amount of the catalyst composition contained in the glycolic acid hydrogenation product;

(C) separating the first raffinate and extract phases;

(D) extracting the first extract phase from step (C) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase from step (C) and a second raffinate phase comprising a minor amount of the catalyst composition contained in the first extract phase; and (E) combining the second extract phase with the aqueous mixture of glycolic acid of step (A).

It is understood that the above process comprises the various embodiments of the glycolic acid hydrogenation product, the catalyst composition, the first extractant, the second extractant, equipment used to carry out the extractions, and the first and second extract phases steps as described previously. For example, the glycolic acid hydrogenation product can comprise about 50 to about 90 weight percent, based on the total weight of the glycolic acid hydrogenation product, ethylene glycol, about 0.5 to about 25 weight percent water, and about 0.5 to about 30 weight percent of one or more reaction by-products described above, and the above catalyst composition.

The first extractant can comprise about 60 to 100 weight percent, based on the total weight of the first extractant, 2-ethylhexanol and about 0 to about 40 weight percent of a hydrocarbon having 5 to 20 carbon atoms. Some representative examples of hydrocarbons include hexane, heptane, octane, decane, benzene, toluene, xylenes, methyl napththalenes, and mixtures thereof. For example, the hydrophobic solvent can comprise 2-ethylhexanol and heptane.

The extraction produces a first raffinate phase comprising a major amount of the ethylene glycol contained in the glycolic acid hydrogenation product and a first extract phase comprising a major amount of the catalyst composition in the glycolic acid hydrogenation product. The raffinate and extract phases may be separated by any phase separation technology known in the art as described hereinabove.

The catalyst composition can be back-extracted from the first extract phase into a solvent mixture that subsequently can be used directly as a reactant in the glycolic acid hydrogenation reaction. Thus, our process also comprises extracting the first extract phase from step (C) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase from step (C) and a second raffinate phase comprising a minor amount of the catalyst composition contained in the first extract phase.

The second extract phase can be passed to a process for the preparation of ethylene glycol by hydrogenation of glycolic acid, glycolate esters, glycolic acid oligomers, or mixtures thereof. The second raffinate phase can be recycled to the first extraction by combining the second raffinate phase with the first extractant. The second raffinate phase can be distilled prior to recycle to produce a hydrophobic solvent distillate that is subsequently combined with the extractant of step (B). Thus, in another embodiment, the process of the invention can further comprise combining the second raffinate phase of step (D) with the first extractant of step (B), or distilling the second raffinate phase of step (D) to produce a hydrophobic solvent distillate and combining the hydrophobic solvent distillate with the first extractant of step (B).

The efficiency of the extraction process of the invention can be measured by a partition coefficient of the phosphine-Ru catalyst composition, abbreviated herein as "P(CAT)," which is defined as the concentration of the metal-ligand complex and non-complexed phosphine in the hydrophobic phase divided by the concentration of the metal-ligand complex and non-complexed phosphine in the hydrophilic phase. The partition coefficient may be determined by analysis of metal content and phosphorus by known methods such as, for example, X-ray analysis.

When the one or more desired products are partitioned between the hydrophilic phase and the hydrophobic phase by the extraction processes of the invention, the P(CAT) value of the metal-ligand complex can be maintained at a level greater than about 1, preferably greater than about 2, and more preferably greater than about 4, depending on the efficiency of the extraction process. If the P(CAT) value is high, Ru or the tridentate phosphine ligand will preferentially distribute into the hydrophobic phase. As noted above, the value of P(CAT) is determined from the concentration of non-complexed, free tridentate phosphine ligand and the ligand complexed with Ru metal.

Similarly, the efficiency of this extraction process also can be measured by a partition coefficient of one or more products present in the glycolic acid hydrogenation product effluent, abbreviated herein as "P(PROD)." P(PROD) is defined as the concentration of the one or more products in the hydrophobic phase divided by the concentration of the one or more products in the hydrophilic phase.

When the one or more desired products are partitioned between the hydrophilic phase and the hydrophobic phase by the forward extraction process of this invention, the P(PROD) value of the products can be maintained at a level less than about 1, preferably less than about 0.75, and more preferably less than about 0.5, depending on the efficiency of the extraction process. If this P(PROD) value is low, the products will preferentially distribute into the hydrophilic phase.

In an embodiment, the extraction process of this invention can be conducted in a manner such that two separation criteria are satisfied. The two criteria are referred to herein as extraction factors and are based on ratios of the partition coefficients defined above. The relationships embodied by the extraction factors include selectivity of the hydrophobic phase for the tridentate phosphine ligand with respect to the product, and selectivity of the hydrophilic phase for the tridentate phosphine ligand with respect to the reaction byproducts.

For example, the extraction factor ("EF") defining selectivity of the hydrophilic phase for the metal-phosphine ligand complex with respect to the one or more products is a partition coefficient ratio, EF=P(CAT)/P(PROD). The EF value for this ratio can be maintained at a level greater than about 2.5. Other values of EF include greater than about 3.0 and greater than about 3.5. If this EF value is high, the extraction selectivity will be high.

FIGS. 1 through 4 represent four, non-limiting embodiments of the instant invention, described herein in detail. In a first embodiment of the invention as laid out in FIG. 1, the effluent stream 15 from Reaction Zone 3, comprising a glycolic acid hydrogenation reaction product, Ru tridentate phosphine ligand complex, and reaction by-products, is optionally combined in Mixing Zone 4 with hydrophilic solvent stream 16, to produce stream 17. Stream 17 is fed countercurrently to Forward Extractor 1, wherein the stream is intimately contacted with hydrophobic solvent stream 12. Two products exit the Forward Extractor 1, the hydrophilic raffinate product stream 18 depleted of catalyst and ligand, and the catalyst-ligand laden, hydrophobic extract stream 1. The catalyst-rich stream 1 is fed countercurrently to a second extraction zone, Back Extractor 2, wherein the stream is intimately contacted with the hydrophilic feed substrate mixture 10, which typically contains a mixture of glycolic acid, mono- and bis-glycolate esters of ethylene glycol, glycolic acid or glycolate ester oligomers, and water. Two products are withdrawn from the Back Extractor 2, the raffinate stream 12 comprising the lean recycle solvent to Forward Extractor 1, and the extract stream 13, comprising the a portion of the feed substrate and recovered catalyst-ligand complex. Extract stream 13 passes to Reaction Zone 3 for transformation into products ultimately exiting the process via stream 18. Any remaining feed substrate needed to meet production requirements in stream 18, but not required for the back extraction of the catalyst enters Reaction Zone 3 via conduit 14.

At times it may be advantageous to modify physical and transport properties the of the hydrophobic solvent stream between the forward and back extraction steps in order to enhance selectivity or recovery of the catalyst-ligand complex in either or both extraction steps. Such a modification may be accomplished by the addition or removal of one or more components comprising the hydrophobic extractant mixture as laid out in the embodiment of the instant invention illustrated in FIG. 2. The effluent stream 15 from Reaction Zone 3, comprising a hydrophilic reaction product, metal catalyst-ligand complex, and reaction by-products, is optionally combined in Mixing Zone 4 with hydrophilic solvent stream 16, to produce stream 17. Stream 17 is fed countercurrently to Forward Extractor 1 wherein the stream is intimately contacted with hydrophobic solvent stream 20. Two products exit the Forward Extractor 1, the hydrophilic raffinate product stream 18 depleted of catalyst and ligand, and the catalyst-ligand laden extract stream 11. The catalyst-rich stream 11 is combined with additional hydrophobic solvent species of stream 19 in Mixing Zone 5, and then fed countercurrently to a second extraction zone, Back Extractor 2, wherein the stream is intimately contacted with the hydrophilic feed substrate mixture 10. Two products are withdrawn from the Back Extractor 2. The raffinate stream 12 comprising the lean hydrophobic recycle solvent is conveyed to Separation Zone 6, wherein the additional hydrophobic solvent species of stream 19 are recovered and the original hydrophobic solvent composition of stream 20 is recycled to Forward Extractor 1. The other product of Back Extractor 2, extract stream 13, comprising the a portion of the feed substrate and recovered catalyst-ligand complex, passes to Reaction Zone 3 for transformation into products. The reaction products ultimately exit the process via stream 18. Any remaining feed substrate needed to meet production requirements in stream 18, but not required for the back extraction of the catalyst enters Reaction Zone 3 via conduit 14.

In the previously described first and second embodiments of the instant invention, conventional extraction, i.e., extractions involving a single solvent feed point, are utilized for the forward and back extraction zones. It may be advantageous, however, to operate the forward or back extraction zones as fractional countercurrent extractions in which additional hydrophobic solvent components or hydrophilic solvent components are introduced as separate feeds. In a third embodiment of the invention as set forth in FIG. 3, the effluent stream 15 from Reaction Zone 3, comprising a glycolic acid hydrogenation reaction product, metal catalyst-ligand complex, and reaction by-products, is optionally combined in Mixing Zone 4 with hydrophilic solvent stream 16, to produce stream 17. Stream 17 is fed countercurrently to Forward Extractor 1 wherein the stream is intimately contacted with hydrophobic solvent stream 12. When operated as a fractional extractor, an additional hydrophilic solvent stream 21, which may comprise the same or similar components to stream 16, is introduced into Forward Extractor 1 above stream 17. Two products exit the Forward Extractor 1, the hydrophilic raffinate product stream 18 depleted of catalyst and ligand, and the catalyst-ligand laden extract stream 11. The purpose of feed stream 21 is to further reduce losses of reaction products into stream 11. The catalyst-rich stream 11 is fed countercurrently to a second extraction zone, Back Extractor 2, wherein the stream is intimately contacted with the hydrophilic feed substrate mixture 10. Two products are withdrawn from the Back Extractor 2, the raffinate stream 12 comprising the lean recycle solvent to Forward Extractor 1, and the extract stream 13, comprising the a portion of the feed substrate (which typically contains a mixture of glycolic acid, mono- and bis-glycolate esters of ethylene glycol, glycolic acid or glycolate ester oligomers, and water) and recovered catalyst-ligand complex. Extract stream 13 passes to Reaction Zone 3 for transformation into products ultimately exiting the process via stream 18. Any remaining feed substrate needed to meet production requirements in stream 18, but not required for the back extraction of the catalyst enters Reaction Zone 3 via conduit 14.

Figure 4:
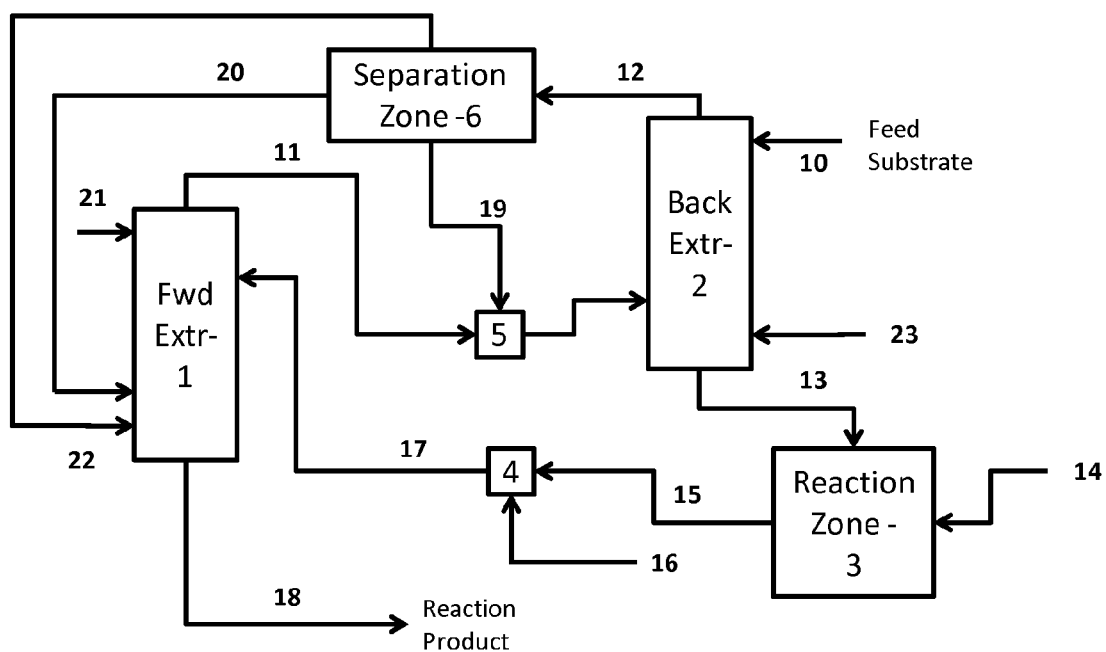
FIG. 4 is a schematic flow diagram for yet another embodiment of the invention in which the extraction process illustrated in FIG. 3 is further modified by additional fractional extraction streams.

The above embodiment may be further modified by additional fractional extraction streams as laid out in the fourth embodiment of the instant invention, FIG. 4. The effluent stream 15 from Reaction Zone 3, comprising a glycolic acid hydrogenation reaction product, metal catalyst-ligand complex, and reaction by-products, is optionally combined in Mixing Zone 4 with hydrophilic solvent stream 16, to produce stream 17. Stream 17 is fed countercurrently to Forward Extractor 1 wherein the stream is intimately contacted with hydrophobic solvent stream 20. When operated as a fractional extractor, an additional hydrophilic solvent stream 21, which may comprise the same or similar components to stream 16, is introduced into Forward Extractor 1 above stream 17. An additional hydrophobic solvent stream 22 may be introduced below feed 21. Two products exit the Forward Extractor 1, the hydrophilic raffinate product stream 18 depleted of catalyst and ligand, and the catalyst-ligand laden extract stream 11. The purposes of feed streams 21 and 22 are to further reduce losses of reaction products into stream 11 and to prevent carryover of hydrophobic components into reaction product 18 respectively. The catalyst-rich stream 11 is combined with additional hydrophobic solvent species of stream 19 in Mixing Zone 5, and then fed countercurrently to a second extraction zone, Back Extractor 2, wherein the stream is intimately contacted with the hydrophilic feed substrate mixture 10, which typically contains a mixture of glycolic acid, mono- and bis-glycolate esters of ethylene glycol, glycolic acid or glycolate ester oligomers, and water. Additional hydrophobic solvent components may be added via stream 23 to Back Extractor 2 in fractional extraction mode. Two products are withdrawn from the Back Extractor 2. The raffinate stream 12 comprising the lean recycle solvent is conveyed to Separation Zone 6, wherein the additional hydrophobic solvent species of streams 19, 22, and 23 are recovered and the original hydrophobic solvent composition of stream 20 is recycled to Forward Extractor 1. The other product of Back Extractor 13, extract stream 13, comprising the a portion of the feed substrate and recovered catalyst-ligand complex, passes to Reaction Zone 3 for transformation into products. The reaction products ultimately exit the process via stream 18. Any remaining feed substrate needed to meet production requirements in stream 18, but not required for the back extraction of the catalyst enters Reaction Zone 3 via conduit 14.

Embodiment A is a process for recovering a homogeneous catalyst, comprising (A) extracting a glycolic acid hydrogenation product, comprising
  (i) about 10 to about 90 weight percent, ethylene glycol, based on the total weight of the glycolic acid hydrogenation product, about 1 to about 50 weight percent water, and about 0.5 to 30 weight percent of one or more reaction by-products selected from glycolic acid, oligomers of glycolic acid, and glycolate esters of ethylene glycol; and
  (ii) a catalyst composition comprising ruthenium and a tridentate ligand comprising at least one phosphine selected from 1,1,1-tris(diaryl-phosphinomethyl)alkanes and 1,1,1-tris(dialkylphosphinomethyl)alkanes;
with a first extractant, comprising
  (i) a hydrophobic solvent selected from alkanols having from 6 to 20 carbon atoms, ketones having from 5 to 20 carbon atoms, esters having from 5 to 20 carbon atoms, ethers having from 5 to 20 carbon atoms, carboxylic acids having from 5 to 20 carbon atoms, and mixtures thereof; and
  (ii) optionally, a hydrophilic solvent;
to form a first raffinate phase comprising a major amount of the ethylene glycol and a minor amount of the catalyst composition contained in the glycolic acid hydrogenation product and a first extract phase comprising a major amount of the catalyst composition and a minor amount of the ethylene glycol contained in the glycolic acid hydrogenation product;

(B) separating the first raffinate and extract phases; and (C) extracting the first extract phase from step (B) with a second extractant comprising water, ethylene glycol, glycolate esters of ethylene glycol, glycolic acid, glycolic acid oligomers, or mixtures thereof to form a second extract phase comprising a major amount of the catalyst composition contained in the first extract phase from step (B) and a second raffinate phase comprising a minor amount of the catalyst composition contained in the first extract phase.

The process of Embodiment A in which the glycolic acid hydrogenation product comprises about 40 to about 90 weight percent ethylene glycol about 0.5 to about 25 weight percent water, and about 0.5 to 15 weight percent of the one or more reaction by-products.

The process of Embodiment A or Embodiment A with any of the intervening features in which the tridentate ligand comprises tris-1,1,1-(diphenylphosphinomethyl)-methane, tris-1,1,1-(diphenylphosphinomethyl)ethane, (2-(butoxymethyl)-2-((diphenyl-phosphino)methyl)propane-1,3-diyl)bis(diphenylphosphine), (2-(benzyloxymethyl)-2-((diphenylphosphino)methyl)propane-1,3-diyl)bis(diphenylphosphine), tris-1,1,1-(diphenylphosphinomethyl)propane, tris-1,1,1-(diphenylphosphinomethyl)butane, tris-1,1,1-(diphenylphosphinomethyl)-2,2-dimethylpropane, tris-1,1,1-(diphenylphosphino-methyl)cyclohexane, tris-1,1,1-(dicyclohexylphosphinomethyl)ethane, tris-1,1,1-(dimethylphosphinomethyl)ethane, tris-1,1,1-(diethylphosphinomethyl)ethane, or mixtures thereof.

The process of Embodiment A or Embodiment A with any of the intervening features in which the tridentate ligand comprises tris-1,1,1-(diphenylphosphino-methyl)ethane.

The process of Embodiment A or Embodiment A with any of the intervening features in which the hydrophobic solvent is selected from 2-ethylhexanol, n-heptanol, n-hexanol, n-octanol, n-nonanol, n-decanol, tetradecanol isomers, methyl isobutylketone, methyl isopropylketone, isobutylisobutyrate, ethyl acetate, n-butyl acetate, isobutylacetate, isopropylacetate, n-propyl acetate, diisopropylether, dibutylether, tertiary-amyl methyl ether, 2-ethylhexanoic acid, and mixtures thereof.

The process of Embodiment A or Embodiment A with any of the intervening features in which the hydrophobic solvent further comprises a hydrocarbon having from 4 to 20 carbon atoms.

The process of Embodiment A or Embodiment A with any of the intervening features in which the hydrocarbon is selected from hexane, heptane, octane, decane, benzene, toluene, xylenes, isoparaffinic mixed hydrocarbons having a boiling range between 90 and 325° C., methyl napththalenes, and mixtures thereof.

The process of Embodiment A or Embodiment A with any of the intervening features in which the first extractant comprises a hydrophilic solvent selected from water, nitriles having from 2 to 3 carbon atoms, alkoxynitriles having from 4 to 6 carbon atoms, alkanols having from 1 to 3 carbon atoms, alkoxyalcohols having from 2 to 6 carbon atoms, pyrrolidones having from 4 to 6 carbon atoms, formamides having from 4 to 6 carbon atoms, sulfoxides having from 4 to 6 carbon atoms, diols having from 2 to 6 carbon atoms, polyols having 2 to 6 carbon atoms, acetic acid, formic acid, α-hydroxy carboxylic acids having from 4 to 6 carbon atoms, glycolic acid oligomers having 2 to 6 repeat units, glycolate esters, and mixtures thereof.

The process of Embodiment A or Embodiment A with any of the intervening features in which the second extractant comprises mono- and diglycolate esters of ethylene glycol The process of Embodiment A or Embodiment A with any of the intervening features in which the tridentate ligand comprises tris-1,1,1-(di-phenylphosphinomethyl)ethane and the hydrophobic solvent comprises 2-ethylhexanol and heptane.

The process of Embodiment A or Embodiment A with any of the intervening features further comprising passing second extract phase to a process for the preparation of ethylene glycol by hydrogenation of glycolic acid, glycolate esters, glycolic acid oligomers, or mixtures thereof to ethylene glycol.

The process of Embodiment A or Embodiment A with any of the intervening features further comprising combining the second raffinate phase of step (C) with the first extractant of step (A), or distilling the second raffinate phase of step (C) to produce a hydrophobic solvent distillate and combining the hydrophobic solvent distillate with the first extractant of step (A).

The process of Embodiment A or Embodiment A with any of the intervening features in which steps (A), (C), or (A) and (C) are carried out by fractional countercurrent extraction.

Embodiment B is the process of Embodiment A in which the glycolic acid hydrogenation product comprises about 40 to about 90 weight percent, ethylene glycol, based on the total weight of the glycolic acid hydrogenation product, about 0.5 to about 25 weight percent water, and about 0.5 to 30 weight percent of one or more reaction by-products selected from glycolic acid, oligomers of glycolic acid, and glycolate esters of ethylene glycol; the catalyst composition comprises ruthenium and tris-1,1,1-(diphenylphosphinomethyl)ethane; and the first extractant comprises about 60 to 100 weight percent, based on the total weight of the first extractant, 2-ethylhexanol, isobutyl isobutyrate, undecanone, methylisobutyl ketone, diisopropyl ether, or mixtures thereof, and about 0 to about 40 weight percent of a hydrocarbon having 5 to 20 carbon atoms.

The process of Embodiment B in which the hydrophobic solvent comprises 2-ethylhexanol and heptane.

The process of Embodiment B in which the hydrophobic solvent comprises 2-ethylhexanol and heptane, and further comprising passing second extract phase to a process for the preparation of ethylene glycol by hydrogenation of glycolic acid, glycolate esters, glycolic acid oligomers, or mixtures thereof to ethylene glycol.

The process of Embodiment B in which the hydrophobic solvent comprises 2- ethylhexanol and heptane, further comprising passing second extract phase to a process for the preparation of ethylene glycol by hydrogenation of glycolic acid, glycolate esters, glycolic acid oligomers, or mixtures thereof to ethylene glycol and further comprising combining the second raffinate phase of step (C) with the first extractant of step (A), or distilling the second raffinate phase of step (C) to produce a hydrophobic solvent distillate and combining the hydrophobic solvent distillate with the first extractant of step (A).

The process of embodiment B as described in any of the preceding, paragraphs in which the glycolic acid hydrogenation product comprises about 50 to about 90 weight percent, based on the total weight of the glycolic acid hydrogenation product, ethylene glycol, about 0.5 to about 25 weight percent water, and about 0.5 to about 30 weight percent of one or more reaction by-products selected from glycolic acid, oligomers of glycolic acid, and glycolate esters of ethylene glycol;

the glycolic acid hydrogenation product is formed by contacting an aqueous mixture comprising glycolic acid, glycolate esters, oligomers of glycolic acid, or mixtures thereof, with hydrogen in the presence of a catalyst composition comprising ruthenium and tris-1,1,1-(diphenylphosphinomethyl)ethane;

the first extractant comprises about 60 to 100 weight percent, based on the total weight of the first extractant, 2-ethylhexanol and about 0 to about 40 weight percent of a hydrocarbon having 5 to 20 carbon atoms; and the process further comprises combining the second extract phase with the aqueous mixture of glycolic acid of step (A).

The invention is further illustrated by the following examples.

EXAMPLES

General

Analyses of glycolic acid hydrogenation products and various extraction phases were carried out by gas chromatography ("GC") using the following procedure. The components from the glycolic acid hydrogenation reaction were first reacted with BSTFA [N,O-bis(trimethylsilyl)trifluoroacetamide] in the presence of pyridine to the corresponding TMS-derivatives including water, which were then separated and quantified by an internal standard (decane) wt % calibrated GC method. The sample to derivatization reagent (BSTFA and pyridine) ratio was 0.1 g:1 ml:0.2 ml in a GC vial, which was heated at 80° C. for 30 minutes to ensure complete derivatization. The GC method used a DB-1301 capillary column or equivalent (6% cyanopropylphenyl/94% dimethylpolysiloxane stationary phase, 60 meters×0.32 mm ID×1.0 um film thickness), a split injector (280° C.), a flame ionization detector (300° C.), helium carrier gas at a constant linear velocity of 27 cm/sec (a Shimadzu GC 2010 or equivalent) or at an initial column head pressure of 17 psi, an oven temperature program of 80° C. initial temp for 6 min, 4° C./min temp ramp rate to 150° C. for 0 min and 10° C./min temp ramp rate to 290° C. for 17.5 min final hold time. A 1-ul aliquot of the prepared sample solution was injected with a split ratio of 40:1. The method provided quantification range of 0.01-100 wt % for each analyte within its separation capability.

Reactor effluent samples were analyzed for sulfur levels using a wavelength dispersive x-ray fluorescence (WDXRF) semi-quantitative application called UNIQUANT™ (UQ). UQ affords standardless XRF analysis of samples. The data were mathematically corrected for matrix differences between calibration standards and samples as well as absorption and enhancement effects; i.e. inter-element effects. Instrument conditions for sulfur analysis were: Line, $K_a$; kV, 40; mA, 60; Filter, none; Collimator Spacing (mm), 150; Crystal, Ge III-C; Peak Angle (2q), 110.6712; Detector, flow; PHD Lower, 35; PHD Upper, 70; Collimator Mask (mm), 30; Peak time (s), 30.

Extractor effluent samples were diluted in isopropyl alcohol to minimize matrix effects and analyzed quantitatively using WDXRF. The WDXRF calibrations were performed using serial dilutions of stock standards prepared wt./wt. and certified using ICP-OES. Instrument conditions for sulfur analysis were: Line, $K_a$; kV, 50; mA, 60; Filter, none; Collimator Spacing (mm), 700; Crystal, Graphite; Peak Angle (2q), 106.4608; −offset, 2.6696; Detector, flow; PHD Lower, 27; PHD Upper, 75; Collimator Mask (mm), 30; −Offset time (s), 10; Peak time (s), 50.

For all extraction examples the partition coefficient for component A is defined as follows:

$$P(A) = \frac{\text{Weight Percent } A \text{ in Hydrophobic phase}}{\text{Weight Percent } A \text{ in Hydrophilic (}EG\text{-rich) Phase}}$$

Selectivity between components A and B is defined as:

$S(AB)=P(A)/P(B)$

Throughout the examples, the following abbreviations are used in the Tables:

| Compound | Abbreviation |
| --- | --- |
| Tris-1,1,1-(diphenylphosphinomethyl)ethane (Structure II) | Triphos |
| (2-(butoxymethyl)-2-((diphenylphosphino)methyl)propane-1,3-diyl)-bis(diphenylphosphine) (Structure (IV)) | BuO-triphos |
| Tris-1,1,1-(diethylphosphinomethyl)ethane (Structure III) | Ethyl-triphos |
| Glycolic Acid | GA |
| Ethylene glycol | EG |
| 1,2-Butanediol | BDO |

| Compound | Abbreviation |
| --- | --- |
| 1,2-Propanediol | PDO |
| 2-Ethylhexanol | 2-EH |
| Isobutyl isobutyrate | IBIB |
| Methyl isobutyl ketone | MIBK |
| Diisopropyl ether | DIPE |

Preparation of Glycolic Acid/Ester Feed and Extractant Mixture—

A mixture glycolic acid and glycolate esters was prepared by heating a mixture of 4000 g of glycolic acid and 1795 grams of ethylene glycol at a temperature of about 100 to about 150° C. under atmospheric pressure while removing the water with a Dean-Stark trap. After approximately 860 g of water were removed, the reaction pressure was lowered to 25 torr and the reaction was continued until a total of 947 g of water were collected. Mixtures of glycolic acid and glycolate esters prepared according to this procedure typically contained about 2 wt % ethylene glycol, about 4 wt % glycolic acid, about 2 wt % glycolic acid dimer, about 32 wt % glycolic acid monoesters of ethylene glycol (about 23 wt % glycolic acid monomer ester of EG, about 8 wt % glycolic acid dimer monoester of EG, and about 2 wt % glycolic acid trimer monoester of EG), and about 60 wt % bis-glycolate esters of EG (about 19 wt % glycolic acid monomer diester of EG, about 11 wt % glycolic acid dimer/glycolic acid monomer diester of EG, about 4 wt % glycolic acid trimer/glycolic acid monomer diester of EG, and about 30 wt % higher glycolic acid oligomer diesters of EG). Because the higher molecular weight glycolic acid oligomer diesters could not be detected by the gas chromatographic method described above, the weight percentages shown for these compounds were estimated by subtracting the total weight percentages of the components detected by GC from 100 wt %. The glycolic acid and ester mixtures prepared by this procedure were used as the feed for glycolic acid hydrogenation reaction and as an extractant for back-extracting the ruthenium catalyst compositions from the various hydrophobic extracts in examples set forth below.

Example 1

Preparation of (2-(butoxymethyl)-2-((diphenylphosphino)-methyl)propane-1,3-diyl)bis(diphenylphosphine) (IV)

Synthesis of pentaerythrityl trichlorohydrin (IX)

A five liter three neck round-bottom flask equipped with an overheard stirrer, a condenser (with a nitrogen purge and a Vigreux column to scrub off any sulfur dioxide), a "Y" connector, with a thermocouple in one side and an addition funnel in the other, was charged with 417 g (3.00 mol) of pentaerythritol and 730 g (9.24 mol) of pyridine. With vigorous stirring, 1134 g (9.24 mol) of thionyl chloride was charged dropwise over a period of 3 hours and 45 minutes and the mixture was heated to 125° C. and held at 125° C. overnight. The brown-yellow solution was cooled to room temperature and 2 L of cold, deionized water was charged with stirring. The precipitate was filtered and washed with 2.5 L of cold, deionized water. The vacuum-dried crude product, (459.7 g), a 1:3.1 mixture of pentaerythrityl trichlorohydrin (VIII) and pentaerythrityltetrachloride (IX) as determined by NMR, was separated using fractional distillation under reduced pressure and recrystallized from cyclohexane to yield 253.5 g of (8).

$^{1}$H NMR of 8 (CDCl$^{3}$): δ 3.74 (s, 3H); 3.66 (s, 6H); 1.72 (br, 1H). $^{13}$C{1H} NMR of 8 (CDCl$^{3}$): δ 61.2, 46.7, 44.0 ppm.

Synthesis of
1-(3-Chloro-2,2-bis(chloromethyl)propoxy)butane
(X)

A 300 mL four neck round-bottom flask equipped with an overheard stirrer, a condenser (with a nitrogen purge) and a thermocouple was charged with 10 g (0.050 mol) of (VIII), 21.68 g (0.16 mol) of 1-bromobutane and 52.50 mL of anhydrous DMSO. The flask was cooled in an ice/water bath and 12.72 g (0.21 mol) of finely ground KOH was charged with vigorous stirring. When no further exotherm was observed, the reaction mixture was heated to 60° C. for 3 hours with stirring. After cooling to room temperature, 225 mL of deionized water was charged slowly. The aqueous phase was extracted with dichloromethane (50 mL) four times. The combined organic layers were washed with 250 mL of 2M HCl, 2×150 mL of deionized water and then dried over Na$_2$SO$_4$. After filtration, the solvent was removed using a rotary evaporator. Product (X) was obtained as a faint yellow liquid. Yield: 11.20 g (0.042 mol, 80%). $^{1}$H NMR (CDCl$_3$): δ 3.65 (s, 6H); 3.46 (s, 2H); 3.44 (t, 2H); 1.56 (m, 2H); 1.36 (m, 2H); 0.92 (m, 3H). $^{13}$C{1H} NMR (CDCl$_3$): δ 71.4, 68.0, 46.2, 44.5, 31.6, 19.3, 13.8 ppm.

Synthesis of (2-(butoxymethyl)-2-((diphenylphosphino)methyl)propane-1,3-diyl)bis(diphenylphosphine) (IV)

A 500 mL three neck round-bottom flask containing 283 g (0.30 mol) of a diethoxymethane (DEM) solution of lithium diphenylphosphide was cooled to −78° C. using a dry ice/acetone bath. To this solution, 23.75 g (0.10 mol) of compound (X) was charged over a period of 30 minutes with an Argon purge. After all of compound (X) was charged, the acetone/dry ice bath was removed, the mixture was allowed to warm to room temperature, and stirred overnight. All volatiles were removed under vacuum, and the residue was extracted with 50 mL of toluene two times. The extract was washed with 50 mL of deionized water three times. The organic phase was dried over Na$_2$SO$_4$, filtered, and the volatiles were removed under vacuum. 49.5 g (about 74% crude yield and 92% purity) of sticky solid was obtained after drying overnight under vacuum. $^{31}$P{1H} NMR (CDCl$_3$): δ −26.3 ppm (s). $^{1}$H NMR (CDCl$_3$): δ 7.50-7.34 (m, 30H); 3.29 (s, 2H); 2.85 (t, 2H); 2.71 (s, 6H); 1.24 m (5H); 0.90 (t, 3H). $^{13}$C{1H} NMR (CDCl$_3$): δ 139.9 (d), 132.9 (d), 128.0 (s), 76.1 (q), 70.3 (s), 42.5 (q), 38.2 (m), 31.4 (s), 19.2 (s), 14.0 (s) ppm.

Example 2

Hydrogenation of Glycolic Acid and Glycolate Esters

A mixture comprising 70 ml ethylene glycol, and 6 mL of the glycolic acid/ester feed mixture described above, 5 weight percent water, and (2-(butoxymethyl)-2-((diphenyl-phosphino)methyl)propane-1,3-diyl)bis(diphenylphosphine) ruthenium diacetate
(referred to herein as "(BuO-triphos)Ru(OAc)$_2$") at a concentration of 100 ppm Ru metal was loaded into a high pressure Hastelloy C autoclave. The autoclave, nominally 100 mL volume, was fitted with a Rushton turbine impeller, baffles, thermowell, gas inlet tube. The reactor vessel was heated electrically to 190° C. by a band heater, with temperature control provided by feedback via a K-type thermocouple in the autoclave thermowell. Pure hydrogen gas (>99.9 volume %) was fed to the autoclave via a Brooks flow controller, with pressure maintained at 124.1 bars gauge (1800 psig). After the initial charge, a stock solution of the glycolic acid/ester feed mixture described above containing 5 weight percent water and (butoxy-triphos)Ru(OAc)$_2$, at a concentration of 100 ppm Ru metal was fed for five hours at a rate of 0.4 mL/min. After five hours, the feed rate was cut to 0.197 mL/min (feed substrate rate of 0.192 ml/min, and the catalyst rate of 0.005 mL/min). Aliquots of reactor material were taken off every five minutes to maintain the liquid level at approximately 71-72.5 mL. The cumulative reactor effluent was found by GC analysis to comprise 85.23 weight percent ethylene glycol, 3.39 weight percent glycolate mono esters of ethylene glycol, 4.5 weight percent water, 0.3 wt % glycolic acid, and 0.5 weight percent glycolate diesters of ethylene glycol. X-ray analysis showed the reactor effluent to comprise 27.9 ppm Ru metal and 23.5 ppm phosphorus content.

Example 3

Hydrogenation of Glycolic Acid and Glycolate Esters

A mixture containing the glycolic acid/ester feed mixture described above, water, and (triphos)Ru(OAc)$_2$, at a concentration of 115 ppm Ru metal was fed continuously at a rate of 0.4 mL/min to a high pressure Hastelloy C autoclave. The ratio of EG diglycolate esters to water was adjusted to achieve 7.5 weight percent to 10 weight percent water in the feed. The autoclave, nominally 100 mL volume, was fitted with a hollow shaft Rushton turbine impeller (for gas introduction and dispersion), baffles, thermowell, gas inlet tube, and sip tube to maintain liquid level at approximately 71 mL and to provide an exit for product effluent. The reactor vessel was heated electrically to 190° C. by a band heater, with temperature control provided by feedback via a K-type thermocouple in the autoclave thermowell. Pure hydrogen gas (>99.9 volume %) was fed to the autoclave via a Brooks flow controller, with pressure maintained at 168.9 bars gauge (2450 psig). The reactor effluent was collected in a Hastelloy vessel. Conditions were maintained for at least 24 hours to establish steady state operation. The reactor effluent was found by GC analysis to comprise 85.71 weight percent ethylene glycol, 1.77 weight percent glycolate mono esters of ethylene glycol, 9.43 weight percent water, 0.4 weight percent glycolic acid, and 0.4 weight percent glycolate diesters of ethylene glycol. X-ray analysis showed the reactor effluent to comprise 111.2 ppm Ru metal and 100.9 ppm phosphorus content.

Example 4

Hydrogenation of Glycolic Acid and Esters

A mixture containing the glycolic acid/ester feed mixture described above, water, and (ethyl-triphos)Ru(OAc)$_2$ at a concentration of about 270 ppm Ru metal was fed continuously at a rate of 0.4 mL/min to a high pressure Hastelloy C autoclave. The ratio of EG diglycolate esters to water was adjusted to achieve less than 1 weight percent water in the feed. The autoclave, nominally 100 mL volume, was fitted with a hollow shaft Rushton turbine impeller (for gas introduction and dispersion), baffles, thermowell, gas inlet tube, and sip tube to maintain liquid level at approximately 71 mL and to provide an exit for product effluent. The reactor vessel was heated electrically to 190° C. by a band heater, with temperature control provided by feedback via a K-type thermocouple in the autoclave thermowell. Pure hydrogen gas (>99.9 volume %) was fed to the autoclave via a Brooks flow controller, with pressure maintained at 168.9 bars gauge (2450 psig). The reactor effluent was collected in a Hastelloy vessel. Conditions were maintained for at least 24 hours to ensure steady state operation. The reactor effluent was found by GC analysis to comprise 99.3 weight percent ethylene glycol, and 0.7 weight percent water. X-ray analysis showed the reactor effluent to comprise 260.5 ppm Ru metal.

Example 5

This Example illustrates the effect of different hydrophobic solvent compositions on the forward and back extraction of the ruthenium catalyst complexes and ethylene glycol. In Experiments 5-1 to 5-11, water was added to the reactor effluent generated in Example 3 to give a water content of 30 weight percent. The resulting mixtures were contacted with a hydrophobic solvent mixture in the composition and S/F ratio specified in Table 1A. Each mixture was held at 60° C., allowed to separate into two clear phases and analyzed by GC and X-ray methods to determine Ru and ethylene glycol content. An identical procedure was repeated for Experiments 5-12 to 5-24, using the reactor effluent generated in Example 2. The resulting partition coefficients and selectivities are summarized in Table 1A.

A portion of the top phase of each extraction Experiment 5-1 to 5-24 was next contacted with the glycolic acid/ester extractant mixture described above at the solvent-feed (S/F) ratio specified in Table 1B. Each mixture was held at 60° C., allowed to separate into two clear phases and analyzed by GC and X-ray methods to determine Ru content in each phase. The resulting partition coefficients are summarized in Table 1B.

TABLE 1A

Extraction of Glycolic Acid Hydrogenation Product

| Ex. | Solvent 1 (wt %) | Solvent 2 (wt %) | Ligand | S/F Ratio | P(Ru) | P(EG) | Select. Ru/EG |
|---|---|---|---|---|---|---|---|
| 5-1 | 2-Ethylhexanol (100%) | | II | 1.00 | 2.80 | 0.16 | 17.5 |
| 5-2 | IBIB (100%) | | II | 1.00 | 0.14 | 0.01 | 13.8 |
| 5-3 | Undecanones (100%) | | II | 1.00 | 0.08 | 0.01 | 8.2 |
| 5-4 | MIBK (100%) | | II | 1.00 | 0.18 | 0.06 | 3.1 |
| 5-5 | DIPE (100%) | | II | 1.00 | 0.02 | 0.00 | 8.3 |
| 5-6 | Heptane (100%) | | II | 1.00 | 0.03 | 0.00 | ∞ |
| 5-7 | 2-Ethylhexanol (90%) | Heptane (10%) | II | 1.00 | 2.01 | 0.13 | 15.5 |
| 5-8 | IBIB (90%) | Heptane (10%) | II | 1.00 | 0.16 | 0.01 | 28.9 |
| 5-9 | undecanones (89%) | Heptane (11%) | II | 1.01 | 0.10 | 0.01 | 14.6 |
| 5-10 | MIBK (90%) | Heptane (10%) | II | 1.00 | 0.14 | 0.02 | 5.7 |
| 5-11 | DIPE (90%) | Heptane (10%) | II | 1.01 | 0.04 | 0.00 | 17.1 |
| 5-12 | 2-Ethylhexanol (100%) | | IV | 1.00 | 8.17 | 0.16 | 51.1 |
| 5-13 | IBIB (100%) | | IV | 1.00 | 0.09 | 0.01 | 11.4 |
| 5-14 | Undecanones (100%) | | IV | 1.00 | 1.79 | 0.01 | 189.1 |
| 5-15 | MIBK (100%) | | IV | 1.00 | 0.13 | 0.04 | 3.2 |
| 5-16 | DIPE (100%) | | IV | 1.00 | 0.07 | 0.00 | 22.2 |
| 5-17 | Heptane (100%) | | IV | 1.00 | 0.04 | 0.00 | ∞ |
| 5-18 | 2-Ethylhexanol (90%) | Heptane (10%) | IV | 1.00 | 9.86 | 0.12 | 82.2 |
| 19 | IBIB (90%) | Heptane (10%) | IV | 1.01 | 0.19 | 0.01 | 21.0 |
| 5-20 | undecanones (91%) | Heptane (9%) | IV | 1.09 | 0.49 | 0.01 | 61.8 |
| 5-21 | MIBK (90%) | Heptane (10%) | IV | 1.00 | 0.32 | 0.02 | 15.1 |
| 5-22 | DIPE (90%) | Heptane (10%) | IV | 1.00 | 0.10 | 0.00 | 43.0 |

TABLE 1B

Recovery of Catalyst from First Extract

| Ex. | Solvent 1 (wt %) | Solvent 2 (wt %) | Ligand Structure | S/F Ratio | P(Ru) |
|---|---|---|---|---|---|
| 5-23 | 2-Ethylhexanol (100%) | | II | 1.00 | 0.41 |
| 5-24 | IBIB (100%) | | II | 1.00 | 1.22 |
| 5-25 | undecanones (100%) | | II | 1.00 | 0.21 |
| 5-26 | MIBK (100%) | | II | 1.00 | 0.30 |
| 5-27 | DIPE (100%) | | II | 1.00 | 0.45 |
| 5-28 | Heptane (100%) | | II | 1.00 | 1.30 |
| 5-29 | 2-Ethylhexanol (90%) | Heptane (10%) | II | 1.00 | 0.23 |
| 5-30 | IBIB (90%) | Heptane (10%) | II | 1.00 | 1.24 |
| 5-31 | Undecanones (89%) | Heptane (11%) | II | 1.00 | 0.44 |
| 5-32 | MIBK (90%) | Heptane (10%) | II | 1.00 | 0.86 |
| 5-33 | DIPE (90%) | Heptane (10%) | II | 1.00 | 0.55 |
| 5-34 | 2-Ethylhexanol (100%) | | IV | 1.00 | 3.03 |
| 5-35 | IBIB (100%) | | IV | 1.00 | 0.66 |
| 5-36 | Undecanones (100%) | | IV | 1.00 | one phase |
| 5-37 | MIBK (100%) | | IV | 1.00 | 0.14 |
| 5-38 | DIPE (100%) | | IV | 1.00 | 6.94 |
| 5-39 | Heptane (100%) | | IV | 1.00 | 0.00 |
| 5-40 | 2-Ethylhexanol (90%) | Heptane (10%) | IV | 1.00 | 1.12 |
| 5-41 | IBIB (90%) | Heptane (10%) | IV | 1.01 | 0.75 |
| 5-42 | Undecanones (91%) | Heptane (9%) | IV | 1.00 | 1.90 |
| 5-43 | MIBK (90%) | Heptane (10%) | IV | 1.01 | 0.18 |
| 5-44 | DIPE (90%) | Heptane (10%) | IV | 1.00 | 9.57 |

Example 6

This example illustrates the effect of water content in the glycolic acid hydrogenation effluent feed mix and the effect of hydrocarbon content of the extractant on extraction of the (BuO-triphos)-Ru catalyst, ethylene glycol, 1,2-butanediol (BDO), and 1,2-propanediol (PDO). In Experiments 6-1 to 6-20, water was added to the reactor effluent generated in Example 2 to give the water content specified in Table 2. In addition, 1 weight percent (on an undiluted reactor effluent basis) each of BDO and PDO was added to the reaction effluent of Example 2. The resulting mixtures were contacted with a solvent mixture comprising 2-ethylhexanol and heptane in the composition and S/F ratio specified in Table 2. Each mixture was held at 60° C., allowed to separate into two clear phases and analyzed by GC and X-ray methods to determine Ru, the partition coefficients (P), ethylene glycol, BDO, and PDO content. The ruthenium, phosphine, ethylene glycol, 1,2-propanediol, and 1,2-butanediol partition coefficients (abbreviated as P(Ru), P(Phos), P(EG), P(PDO), and P(BDO)) are summarized in Table 2.

triphos-Ru catalyst, ethylene glycol, 1,2-butanediol (BDO), and 1,2-propanediol (PDO). In Experiments 7-1 to 7-20, water was added to the reactor effluent generated in Example 3 to give the water content specified in Table 3. In addition, 1 weight percent (on an undiluted reactor effluent basis) each of BDO and PDO was added to the effluent of Example 3. The resulting mixtures were contacted with a solvent mixture comprising 2-ethylhexanol and heptane in the composition and S/F ratio specified in Table 3. Each mixture was held at 60° C., allowed to separate into two clear phases and analyzed by GC and X-ray methods to determine Ru, P, ethylene glycol, BDO, and PDO content. The ruthenium, phosphine, ethylene glycol, 1,2-propanediol, and 1,2-butanediol partition coefficients (abbreviated as P(Ru), P(Phos), P(EG), P(PDO), and P(BDO)) are summarized in Table 3.

TABLE 2

| Ex. | S/F Ratio | Wt % Water in Feed Mix | Wt % Heptane in Solvent Mix | P(Ru) | P(Phos) | P(EG) | P(PDO) | P(BDO) |
|---|---|---|---|---|---|---|---|---|
| 6-1 | 0.99 | 9.89% | 0.0% | 3.24 | 4.16 | 0.46 | 0.63 | 0.87 |
| 6-2 | 1.00 | 14.00% | 0.0% | 2.40 | 6.41 | 0.31 | 0.50 | 0.79 |
| 6-3 | 0.99 | 23.71% | 0.0% | 5.51 | 8.46 | 0.21 | 0.37 | 0.68 |
| 6-4 | 1.00 | 33.25% | 0.0% | 8.17 | 48.73 | 0.16 | 0.31 | 0.63 |
| 6-5 | 1.00 | 9.89% | 10.0% | 2.05 | 2.31 | 0.32 | 0.48 | 0.72 |
| 6-6 | 0.99 | 14.00% | 10.0% | 2.01 | 2.40 | 0.23 | 0.39 | 0.65 |
| 6-7 | 1.01 | 23.71% | 10.0% | 3.30 | 6.55 | 0.16 | 0.31 | 0.58 |
| 6-8 | 1.00 | 33.25% | 10.0% | 9.86 | 12.78 | 0.12 | 0.25 | 0.53 |
| 6-9 | 1.00 | 9.89% | 15.1% | 1.45 | 1.75 | 0.26 | 0.41 | 0.64 |
| 6-10 | 1.01 | 14.00% | 15.1% | 1.96 | 2.44 | 0.20 | 0.35 | 0.58 |
| 6-11 | 1.00 | 23.71% | 15.1% | 3.71 | 5.06 | 0.14 | 0.27 | 0.53 |
| 6-12 | 1.00 | 33.25% | 15.1% | 4.93 | 21.89 | 0.11 | 0.23 | 0.48 |
| 6-13 | 1.00 | 9.89% | 20.0% | 1.26 | 1.21 | 0.22 | 0.36 | 0.58 |
| 6-14 | 0.99 | 14.00% | 20.0% | 1.64 | 1.92 | 0.18 | 0.31 | 0.54 |
| 6-15 | 1.01 | 23.71% | 20.0% | 3.70 | 6.10 | 0.13 | 0.25 | 0.49 |
| 6-16 | 0.99 | 33.25% | 20.0% | 5.15 | 11.07 | 0.10 | 0.21 | 0.45 |
| 6-17 | 0.99 | 9.89% | 30.0% | 0.87 | 1.07 | 0.16 | 0.27 | 0.45 |
| 6-18 | 1.00 | 14.00% | 30.0% | 1.10 | 1.57 | 0.14 | 0.25 | 0.45 |
| 6-19 | 1.00 | 23.71% | 30.0% | 3.74 | 3.26 | 0.10 | 0.20 | 0.39 |
| 6-20 | 1.00 | 33.25% | 30.0% | 3.82 | 14.56 | 0.08 | 0.17 | 0.37 |

Example 7

This example illustrates the effect of water content in the glycolic acid hydrogenation effluent feed mix and the effect of hydrocarbon content of the extractant on extraction of the

TABLE 3

| Ex. | S/F Ratio | Wt % Water in Feed Mix | Wt % Heptane in Solvent Mix | P(Ru) | P(Phos) | P(EG) | P(PDO) | P(BDO) |
|---|---|---|---|---|---|---|---|---|
| 7-1 | 0.99 | 9.2% | 0% | 2.19 | 2.02 | 0.56 | 0.72 | 0.93 |
| 7-2 | 1.00 | 13.5% | 0% | 1.44 | 1.51 | 0.34 | 0.50 | 0.79 |
| 7-3 | 1.00 | 22.5% | 0% | 1.87 | 1.91 | 0.21 | 0.36 | 0.68 |
| 7-4 | 1.00 | 30.4% | 0% | 2.80 | 3.23 | 0.16 | 0.30 | 0.64 |
| 7-5 | 1.00 | 9.2% | 10% | 0.87 | 0.81 | 0.32 | 0.47 | 0.71 |
| 7-6 | 1.00 | 13.5% | 10% | 0.99 | 0.94 | 0.25 | 0.41 | 0.68 |
| 7-7 | 1.00 | 22.5% | 10% | 1.29 | 1.45 | 0.17 | 0.31 | 0.60 |
| 7-8 | 1.00 | 30.4% | 10% | 2.01 | 2.13 | 0.13 | 0.25 | 0.55 |
| 7-9 | 1.00 | 9.2% | 15% | 0.67 | 0.70 | 0.25 | 0.39 | 0.62 |
| 7-10 | 1.00 | 13.5% | 15% | 0.79 | 1.49 | 0.20 | 0.34 | 0.57 |
| 7-11 | 1.00 | 22.5% | 15% | 1.12 | 1.13 | 0.15 | 0.26 | 0.54 |
| 7-12 | 1.01 | 30.4% | 15% | 1.87 | 1.82 | 0.11 | 0.22 | 0.49 |
| 7-13 | 0.89 | 9.2% | 20% | 0.58 | 0.59 | 0.22 | 0.35 | 0.58 |
| 7-14 | 1.00 | 13.5% | 20% | 0.69 | 0.69 | 0.19 | 0.32 | 0.56 |
| 7-15 | 1.00 | 22.5% | 20% | 1.02 | 1.03 | 0.13 | 0.23 | 0.47 |
| 7-16 | 1.01 | 30.4% | 20% | 1.59 | 1.70 | 0.10 | 0.20 | 0.43 |
| 7-17 | 1.00 | 9.2% | 30% | 0.38 | 0.41 | 0.16 | 0.27 | 0.45 |
| 7-18 | 1.01 | 13.5% | 30% | 0.49 | 0.49 | 0.13 | 0.24 | 0.44 |
| 7-19 | 1.00 | 22.5% | 30% | 0.75 | 0.77 | 0.10 | 0.19 | 0.39 |
| 7-20 | 1.00 | 30.4% | 30% | 1.21 | 0.64 | 0.08 | 0.16 | 0.36 |

The hydrophobic solvent system described herein for the extraction of the catalyst-ligand complex from a hydrogenated glycolic acid stream also may be used for the extractive separation of diol hydrogenation by-products from a hydrogenated glycolic acid stream comprising ethylene glycol. As shown by the partition coefficients shown in Tables 2 and 3, the extraction process of the instant invention is useful for separating three- and four-carbon diols, e.g., 1,2-propanediol, and 1,2-butanediol, from ethylene glycol. Because of the lower capacity and selectivity for the extraction of diols, the solvent to feed ratio and/or number of extraction stages must be increased over that required for extraction of the catalyst-ligand complex.

Example 8

This Example illustrates extractive recovery of a (BuO-triphos)-Ru catalyst from a glycolic acid hydrogenation reaction effluent. Water was added to the reactor effluent generated in Example 2 so that the resulting mixture contained about 31 weight percent water. This feed mixture was subjected to cross-flow batch extractions at 60° C. using a solvent comprised of a mixture of 90 weight percent 2-ethylhexanol and 10 weight percent heptane as modifier. In Example 8-1, one extraction was carried out. In Example 8-2, three cross flow extractions were completed in the following fashion. The aqueous feed mixture was contacted with the specified solvent mixture at the given solvent to feed ratio, and the resulting aqueous ethylene glycol phase from the first extraction step was contacted with another portion of fresh solvent. This sequence was repeated an additional time for a total of three cross flow extractions. In both Examples 8-1 and 8-2, the extract and raffinate streams from each cross flow extraction were subjected to gas chromatography and X-ray analysis for ruthenium and phosphorus to determine the compositions of the phases. The feed conditions for each set of extractions, the resulting Ru and P recovery into the extract phase, and the partition coefficient for ethylene glycol are summarized in Table 4 below.

Example 9

This example illustrates back extraction of a (BuO-triphos)-Ru catalyst from the catalyst-rich extract mixture of Example 8-1 using the glycolic acid/ester extractant mixture described above. The catalyst-rich extract mixture of Example 8-1, containing 8.6 weight percent heptane in 2-ethylhexanol, was divided into four portions. Additional heptane was added to three of the portions as set forth in Table 5. Each of these portions was subjected to cross-flow batch extractions at 60° C. using the glycolic acid/ester extractant mixture described above at the solvent to feed ratio specified in Table 5. The resulting heptane/2-ethylhexanol phase from the first extraction step was contacted with another portion of fresh extractant. In all experiments the extract and raffinate streams from each cross flow extraction were subjected to gas chromatography and X-ray analysis for ruthenium and phosphorus to determine the compositions of the phases. The feed conditions for each set of extractions and the resulting Ru and P recovery into the glycolate acid/ester extract phase are summarized in Table 5 below.

TABLE 5

| Ex. | Wt % 2-EH in Feed | Wt % Heptane in Feed | T, ° C. | No. of Extraction Stages | S/F Ratio per Stage | % Recov. Ru | % Recov Phos |
| --- | --- | --- | --- | --- | --- | --- | --- |
| 9-1 | 91.4% | 8.6% | 60 | 2 | 0.71 | 74% | 85% |
| 9-2 | 80.4% | 19.6% | 60 | 2 | 0.71 | 83% | 89% |
| 9-3 | 71.8% | 28.2% | 60 | 2 | 0.72 | 94% | 92% |
| 9-4 | 62.5% | 37.5% | 60 | 2 | 0.71 | 99% | 96% |

Example 10

This example illustrates extractive recovery of a triphos-Ru catalyst from a glycolic acid hydrogenation reaction effluent. Water was added to the reactor effluent generated in Example 3 to give a feed mixture containing about 30 weight percent water. This feed mixture was subjected to cross-flow batch extractions at 60° C. using a solvent comprised of a mixture of 89.9 weight percent 2-ethylhexanol and 10.1 weight percent heptane. In Example 10-1, one extraction was carried out. In Example 10-2, three cross flow extractions were completed in the following fashion. The aqueous hydrogenation reaction effluent feed mixture was contacted with the specified solvent mixture at the given solvent to feed ratio, and the resulting aqueous ethylene glycol phase from the first extraction step was contacted with another portion of fresh solvent. This sequence was repeated an additional time for a total of three cross flow extractions. In both Examples 10-1 and 10-2, the extract and raffinate streams from each cross flow extraction were subjected to gas chromatography and X-ray analysis for ruthenium and phosphorus to determine the compositions of the phases. The feed conditions for each set of extractions, the

TABLE 4

| Ex. | Wt % 2-EH Alcohol in Solvent | Wt % Heptane in Solvent | Wt % Water in Feed | T, ° C. | No. Extr. Stages | S/F Ratio per Stage | % Ru Recov | % Phos Recov | P(EG) |
| --- | --- | --- | --- | --- | --- | --- | --- | --- | --- |
| 8-1 | 90.0% | 10.0% | 31% | 60 | 1 | 1.00 | 82% | 97% | 9.5 |
| 8-2 | 90.0% | 10.0% | 31% | 60 | 3 | 0.35 | 92% | 100% | 9.0 | resulting Ru and phosphorus recovery into the extract phase, and the partition coefficient for ethylene glycol, P(EG), are summarized in Table 6 below.

TABLE 6

| Ex. | Wt % 2-EH in Solvent | Wt % Heptane in Solvent | Wt % Water in Feed | T, ° C. | No. of Extract. Stages | S/F Ratio per Stage | % Recov Ru | % Recov Phos | P(EG) |
|---|---|---|---|---|---|---|---|---|---|
| 10-1 | 89.9% | 10.1% | 30% | 60 | 1 | 1.00 | 54% | 59% | 8.7 |
| 10-2 | 89.9% | 10.1% | 30% | 60 | 3 | 0.35 | 82% | 81% | 7.9 |

Example 11

This example illustrates back extraction of a triphos-Ru catalyst from the catalyst-rich extract mixture of Experiment 10-1 using the glycolic acid/ester extractant mixture described above. The catalyst-rich extract mixture of Experiment 10-1, comprising 7.1 weight percent heptane in 2-ethylhexanol, was divided into four portions, and additional heptane was added to three of the portions as outlined in Table 7. Each of these portions was subjected to cross-flow batch extractions at 60° C. using the glycolic acid/ester extractant mixture described above at the solvent to feed ratio specified in Table 7. The resulting heptane/2-ethylhexanol phase from the first extraction step was contacted with another portion of fresh extractant. In all experiments the extract and raffinate streams from each cross flow extraction were subjected to gas chromatography and X-ray analysis for ruthenium and phosphorus to determine the compositions of the phases. The feed conditions for each set of extractions and the resulting Ru and P recovery into the glycolic acid/ester extract phase are summarized in Table 7 below.

TABLE 7

| Ex. | Wt % 2-EH in Feed | Wt % Heptane in Feed | T, ° C. | No. of Extr. Stages | S/F Ratio per Stage | % Recov Ru | % Recov Phos |
|---|---|---|---|---|---|---|---|
| 11-1 | 92.9% | 7.1% | 60 | 2 | 0.71 | 94.3% | 91% |
| 11-2 | 81.1% | 18.9% | 60 | 2 | 0.71 | 95.1% | 94% |
| 11-3 | 73.5% | 26.5% | 60 | 2 | 0.72 | 96.5% | 89% |
| 11-4 | 63.8% | 36.2% | 60 | 2 | 0.71 | 96.7% | 87% |

Example 12

This example illustrates extractive recovery of an (ethyl-triphos)-Ru catalyst from a glycolic acid hydrogenation reaction effluent. Various levels of water were added to the reactor effluent generated in Reaction Example 4 as shown in Table 8. These feed mixtures were subjected to a cross-flow batch extraction at 60° C. using an extractant (solvent) containing a mixture of 90 weight percent 2-ethylhexanol and 10 weight percent heptane. The extract and raffinate streams from each cross flow extraction were subjected to gas chromatography and X-ray analysis for ruthenium to determine the compositions of the phases. The feed conditions for each set of extractions, the resulting Ru recovery into the extract phase, and the partition coefficient for ethylene glycol are summarized in Table 8 below.

TABLE 8

| Ex. | Wt % 2-EH in Solvent | Wt % Heptane in Solvent | Wt % Water in Feed | T, ° C. | No. of Extraction Stages | S/F Ratio per Stage | % Recov Ru | % Recov Phos |
|---|---|---|---|---|---|---|---|---|
| 12-1 | 90% | 10% | 6.30% | 60 | 1 | 1.00 | 33.2% | 0.34 |
| 12-2 | 90% | 10% | 24.95% | 60 | 1 | 1.00 | 10.4% | 0.18 |
| 12-3 | 90% | 10% | 44.93% | 60 | 1 | 1.00 | 5.8% | 0.06 |

Example 13

This example illustrates back extraction of an (ethyl-triphos)-Ru catalyst from the catalyst-rich extract mixtures of Example 12 using the glycolic acid/ester extractant mixture described above. The catalyst-rich extract mixtures of Experiment 12-1, 12-2, and 12-3 were divided into four portions, and additional heptane was added to three of the portions as outlined in Table 9. Each of these portions was subjected to a cross-flow batch extractions at 60° C. using the glycolic acid/ester extractant mixture at the solvent to feed ratio specified in Table 9. In all experiments the extract and raffinate streams from each cross flow extraction were subjected to gas chromatography and X-ray analysis for ruthenium to determine the compositions of the phases. The feed conditions for each set of extractions and the resulting Ru recovery into the glycolic acid/ester extract phase are summarized in Table 9 below.

TABLE 9

| Ex. | Extract Sample | Wt % 2-EH in Feed | wt % Heptane in Feed | T, ° C. | Number of Extr. Stages | S/F Ratio per Stage | % Recov. of Ru |
|---|---|---|---|---|---|---|---|
| 13-1 | 12-1 | 93.7% | 6.4% | 60 | 1 | 1.00 | 97.6% |
| 13-2 | 12-1 | 83.5% | 16.5% | 60 | 1 | 1.00 | 99.9% |
| 13-3 | 12-1 | 72.6% | 27.4% | 60 | 1 | 1.00 | 100.0% |
| 13-4 | 12-1 | 62.3% | 37.7% | 60 | 1 | 1.01 | 100.0% |
| 13-5 | 12-2 | 91.4% | 8.6% | 60 | 1 | 1.00 | 96.3% |
| 13-6 | 12-2 | 81.4% | 18.6% | 60 | 1 | 1.00 | 100.0% |
| 13-7 | 12-2 | 70.7% | 29.3% | 60 | 1 | 0.99 | 100.0% |
| 13-8 | 12-2 | 60.9% | 39.1% | 60 | 1 | 1.00 | 100.0% |
| 13-9 | 12-3 | 92.7% | 7.3% | 60 | 1 | 0.99 | 96.5% |
| 13-10 | 12-3 | 82.7% | 17.3% | 60 | 1 | 1.00 | 100.0% |
| 13-11 | 12-3 | 71.8% | 28.2% | 60 | 1 | 1.01 | 100.0% |
| 13-12 | 12-3 | 61.9% | 38.1% | 60 | 1 | 1.00 | 100.0% |

Example 14

This example illustrates back extraction of a BuO-triphos Ru catalyst from a catalyst-rich extract mixture with various hydrophilic solvents. The catalyst-rich extract mixture was prepared by adding water to a portion of the reactor effluent generated in Example 2 so that the resulting mixture contained about 31 weight percent water. This feed mixture was subjected to a cross-flow batch extraction at 60° C. using an extractant containing a mixture of 90 weight percent 2-ethylhexanol and 10 weight percent decane as modifier. The solvent to feed weight ratio was 1.03:1. The top phase, a catalyst-rich extract mixture, comprising 9.3 weight percent decane in 2-ethylhexanol, other extracted components, and 86% of the BuO-triphos Ru ligand complex present in the original feed, was divided into nine portions, and additional decane was added to six of the portions as outlined in Table 10. Each of these portions was subjected to a cross-flow batch extractions, at the specified temperature and solvent to feed weight ratio, using a hydrophilic solvent containing one of the following: 1) water; 2) glycolic acid ester dimers and related oligomers; 3) glycolic acid, 85 weight percent in water. In all experiments, the extract and raffinate streams from each cross flow extraction were subjected to gas chromatography and X-ray analysis for ruthenium to determine the compositions of the phases. Results are summarized in Table 10 below.

TABLE 10

| Ex. | T, ° C. | Solvent | S/F Ratio | % Decane in Solvent Mix | P(Ru) | P(EG) |
|---|---|---|---|---|---|---|
| 14-1 | 60° C. | water | 1.00 | 9.3% | 16.67 | 0.04 |
| 14-2 | 60° C. | water | 1.00 | 24.4% | 33.33 | 0.03 |
| 14-3 | 60° C. | water | 1.01 | 39.4% | 12.50 | 0.02 |
| 14-4 | 100° C. | GA dimers | 1.00 | 9.3% | 0.25 | Not meas. |
| 14-5 | 100° C. | GA dimers | 1.01 | 24.5% | 0.22 | Not meas. |
| 14-6 | 100° C. | GA dimers | 1.00 | 39.5% | 0.36 | Not meas. |
| 14-7 | 60° C. | 85% GA | 1.00 | 9.3% | 1.43 | 0.30 |
| 14-8 | 60° C. | 85% GA | 1.00 | 24.5% | 0.59 | 0.25 |
| 14-9 | 60° C. | 85% GA | 1.00 | 39.6% | 0.18 | 0.14 |

Example 15

This example illustrates back extraction of a triphos Ru catalyst from a catalyst-rich hydrophobic extract mixture with various hydrophilic solvents. The catalyst-rich extract mixture was prepared as follows. Water was added to a portion of the reactor effluent generated in Example 3 so that the resulting mixture contained about 31 weight percent water. This feed mixture was subjected to a cross-flow batch extraction at 60° C. using a extractant containing a mixture of 90 weight percent 2-ethylhexanol and 10 weight percent decane as modifier. The solvent to feed weight ratio was 1.03:1. The top phase, a catalyst-rich extract mixture, comprising 9.3 weight percent decane in 2-ethylhexanol, other extracted components, and 59% of the triphos-Ru ligand complex present in the original feed, was divided into nine portions, and additional decane was added to six of the portions as outlined in Table 11. Each of these portions was subjected to a cross-flow batch extractions, at the specified temperature and solvent to feed weight ratio, using a hydrophilic solvent comprised of one of the following: 1) water; 2) glycolic acid ester dimers and related oligomers; 3) glycolic acid, 85 weight percent in water. In all experiments the extract and raffinate streams from each cross flow extraction were subjected to gas chromatography and X-ray analysis for ruthenium to determine the compositions of the phases. Results are summarized in Table 10 below.

TABLE 11

| Ex. | T, °C. | Solvent | S/F Ratio | % Decane in Solvent Mix | P(Ru) | P(EG) |
|---|---|---|---|---|---|---|
| 15-1 | 60° C. | water | 1.00 | 9.3% | ∞ | 0.04 |
| 15-2 | 60° C. | water | 1.00 | 24.5% | 50.00 | 0.03 |
| 15-3 | 60° C. | water | 1.00 | 39.5% | 14.29 | 0.02 |
| 15-4 | 100° C. | GA dimers | 1.00 | 9.3% | 3.33 | Not meas. |
| 15-5 | 100° C. | GA dimers | 1.00 | 24.6% | 1.75 | Not meas. |
| 15-6 | 100° C. | GA dimers | 1.00 | 39.6% | 3.85 | Not meas. |
| 15-7 | 60° C. | 85% GA | 0.99 | 9.3% | 14.29 | 0.40 |
| 15-8 | 60° C. | 85% GA | 1.00 | 24.7% | 4.35 | 0.24 |
| 15-9 | 60° C. | 85% GA | 1.00 | 30.00% | 1.59 | 0.17 |

Example 16

Figure 2:
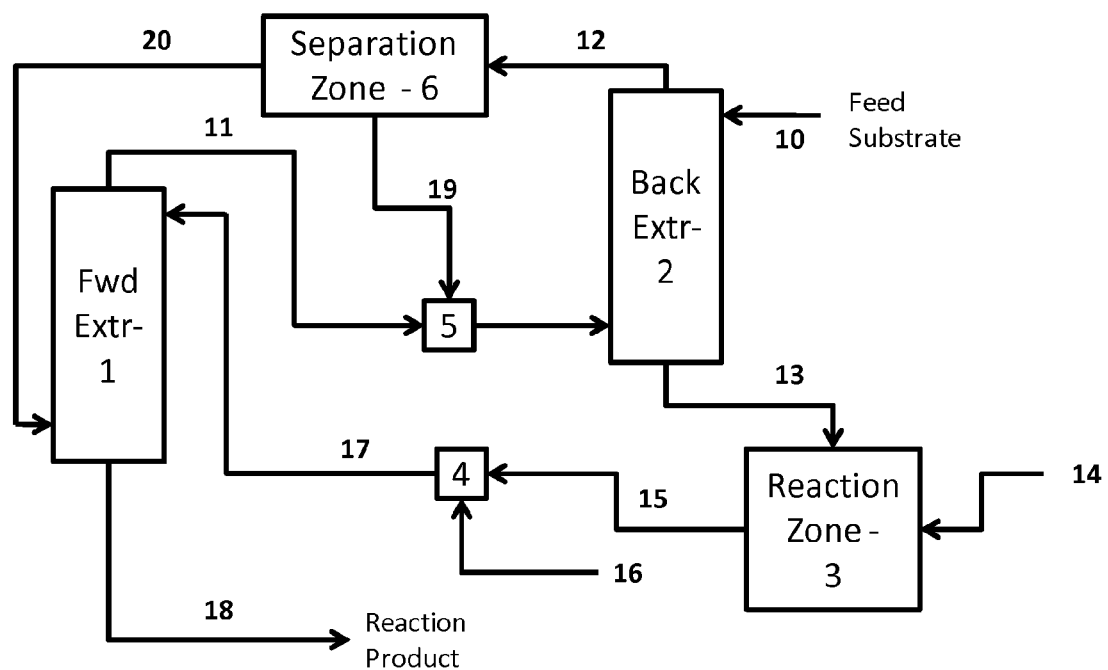
FIG. 2 is a schematic flow diagram for another embodiment of the invention in which a hydrophobic solvent from the back extractor is recovered in a separation zone and combined with the catalyst-rich hydrophobic extract from the forward extractor.
Figure 3:
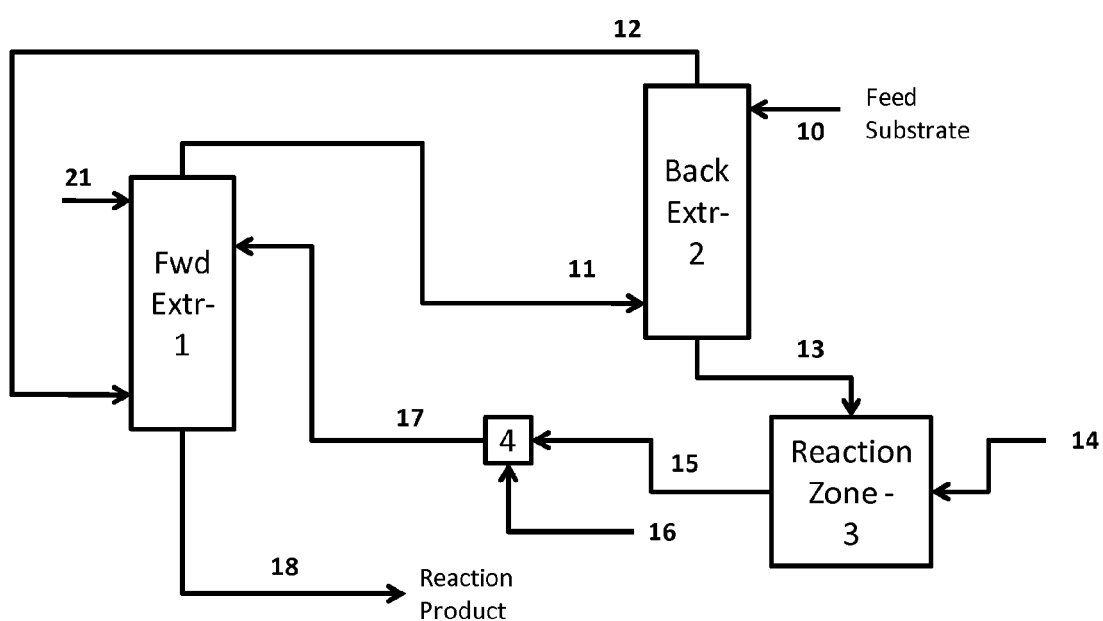
FIG. 3 is a schematic flow diagram illustrating another embodiment of the invention in which the forward extraction zone is operated as a fractional countercurrent extraction.

This example illustrates a computer-generated material balance for an embodiment of the instant invention that is illustrated in FIG. 2 for the extractive recovery of the triphos Ru ligand complex from a glycolic acid hydrogenation reaction effluent. The glycolic acid hydrogenation reaction effluent composition taken from Example 10. Stream ID's are as shown in FIG. 2. The extractant stream 20 for the forward extraction contains 10 weight percent heptane in 2-ethylhexanol. The feed substrate extractant stream 10 for the back extraction is a mixture of glycolic acid and glycolate esters of ethylene glycol as described above for glycolic acid/ester extractant mixture and exemplified in Example 11. The remainder of the extractant stream enters Reaction Zone 3 via stream 14. The system was modeled using the Kremser method, as described in Treybal, *Liquid Extraction,* $2^{nd}$ Ed., McGraw Hill, 1963, pp. 248-252, for both the forward and back extractions, with partition coefficients correlated from the data of Examples 3 and 7. Material balance data is given in Table 12A. Heptane was added to the extract stream 11 of Forward Extractor 1 via stream 19 and later removed from the raffinate stream 12 of Back Extractor 2 via Separation Zone 6. The reaction product stream 18 comprises 46034 kg/hr of ethylene glycol. A summary of the resulting extractor column design parameters are given in Table 12B.

TABLE 12A

Calculated Material Balances for a Recovery Process Illustrated by FIG. 2 (All values in kg/hr)

| Stream ID | Ru | P | EG | $H_2O$ | 2-EH | Heptane | EG glycolates | Total |
|---|---|---|---|---|---|---|---|---|
| 10 | | | 1238 | 236 | | | 43134 | 44608 |
| 11 | 3.84 | 3.85 | 7533 | 1587 | 69253 | 7695 | 220 | 87040 |
| 12 | 0.00 | 0.00 | 50 | 1 | 68475 | 19773 | | 88565 |
| 13 | 3.84 | 3.84 | 8721 | 1822 | 778 | 11 | 43833 | 55173 |
| 14 | | | 35 | 7 | | | 3629 | 3671 |
| 15 | 3.85 | 3.85 | 53568 | 17562 | | | 2158 | 76948 |
| 16 | | | | 0 | | | | 0 |
| 17 | 3.85 | 3.85 | 53568 | 17562 | 0 | 0 | 2158 | 76948 |
| 18 | 0.00 | 0.00 | 46034 | 15976 | 0 | 0 | 1939 | 66857 |
| 19 | | | | | | 12089 | | 12089 |
| 20 | | | | | 69253 | 7695 | | 76948 |

TABLE 12B

Extractor Column Design Parameters

| | S/F Ratio | Stages | Diameter (M) | % Ru Recov | Total Flow, (kg/hr) | EG Prod. (kg/hr) | % EG Glycolates to Back Extr | Heptane Distilled, (kg/hr) |
|---|---|---|---|---|---|---|---|---|
| Fwd | 1.00 | 12 | 2.6 | 99.92% | 153897 | 46034 | | |
| Back | 0.45 | 8 | 2.6 | 99.99% | 143738 | | 92% | 12089 |

Example 17

This example illustrates a computer-generated material balance for another embodiment of the instant invention that can be illustrated in FIG. 2 for the extractive recovery of a BuO-triphos Ru catalyst from a glycolic acid hydrogenation effluent as exemplified in Example 8. Stream ID's are as shown in FIG. 2. The extractant stream 20 for the forward extraction is 10 weight percent heptane in 2-ethylhexanol. The feed substrate extractant stream 10 for the back extraction is a mixture of glycolic acid and glycolate esters of ethylene glycol as exemplified in Example 9 and by the glycolic acid/ester extractant mixture described above. The remainder of the bis-glycolates enters Reaction Zone 3 via stream 14. The system was modeled using the Kremser method, as described in Treybal, *Liquid Extraction*, $2^{nd}$ Ed., McGraw Hill, 1963, pp. 248-252, for both the forward and back extractions, with partition coefficients correlated from the data of Examples 6 and 10. Material balance data is given in Table 13A. Heptane was added to the extract stream 11 of Forward Extractor 1 via stream 19 and later removed from the raffinate stream 12 of Back Extractor 2 via Separation Zone 6. The reaction product stream 18 comprises 46034 kg/hr of ethylene glycol. A summary of the resulting extractor column design parameters are given in Table 13B.

TABLE 13A

Calculated Material Balances for a Recovery Process Illustrated by FIG. 2 (All values in kg/hr)

| Steam ID | Ru | P | EG | H2O | 2-EH | Heptane | EG glycolates | Total |
|---|---|---|---|---|---|---|---|---|
| 10 | | | 1145 | 218 | | | 39874 | 41236 |
| 11 | 3.51 | 3.51 | 2819 | 597 | 25554 | 2839 | 82 | 32177 |
| 12 | 0.00 | 0.00 | 0 | 0 | 24611 | 10932 | | 35543 |
| 13 | 3.51 | 3.51 | 3964 | 815 | 943 | 20 | 40234 | 45983 |
| 14 | | | 131 | 25 | | | 13705 | 13861 |
| 15 | 3.51 | 3.51 | 48854 | 16017 | | | 1969 | 70177 |
| 16 | | | | 0 | | | | 0 |
| 17 | 3.51 | 3.51 | 48854 | 16017 | 0 | 0 | 1969 | 70177 |
| 18 | 0.00 | 0.00 | 46034 | 15420 | 0 | 0 | 1886 | 66393 |
| 19 | | | | | | 8112 | | 8112 |
| 20 | | | | | 25554 | 2839 | | 28394 |

TABLE 13B

Extractor Column Design Parameters

| | S/F Ratio | Stages | Diameter (M) | % Ru Recov | Total Flow (kg/hr) | EG Prod. (kg/hr) | % Bis Glycolates to Back Extr | Heptane Distilled (kg/hr) |
|---|---|---|---|---|---|---|---|---|
| Fwd | 0.40 | 8 | 2.0 | 99.92% | 98570 | 46034 | | |
| Back | 1.02 | 12 | 1.9 | 99.99% | 81526 | | 75% | 8112 |

Example 18

This example illustrates a computer-generated material balance for an embodiment of the instant invention that can be illustrated in FIG. 4 for the extractive recovery of a triphos Ru catalyst from a glycolic acid hydrogenation product effluent as exemplified in Example 10. Stream ID's are as shown in FIG. 4. The extractant stream 20 for the forward extraction is 15 weight percent heptane in 2-ethylhexanol at a solvent to feed ratio of 0.70. Water wash enters Forward Extractor 1 via stream 21 at a ratio of 0.2 kg per kg of solvent. The feed substrate extractant stream 10 for the back extraction is a mixture of glycolic acid and glycolate esters of ethylene glycolates as exemplified in Example 7 and by the glycolic acid/ester extractant mixture described above. The system was modeled using the Kremser method, as described in Treybal, *Liquid Extraction*, $2^{nd}$ Ed., McGraw Hill, 1963, pp. 248-252, for both the forward and back extractions, with partition coefficients correlated from the data of Examples 7 and 11. Material balance data is given in Table 14A. No heptane was added to the extract stream 11 of Forward Extractor 1. The reaction product stream 18 comprises 77,369 kg/hr of ethylene glycol. A summary of the resulting extractor column design parameters are given in Table 14B.

TABLE 14A

Calculated Material Balances for a Recovery Process Illustrated by FIG. 4 (All values in kg/hr)

| Stream ID | Ru | P | EG | H₂O | 2-EH | Heptane | EG glycolates | Other Polar Compunds |
|---|---|---|---|---|---|---|---|---|
| 10 | 0.000 | 0.000 | 5,471 | 3,230 | 0 | 0 | 54,034 | 10,322 |
| 11 | 4.518 | 4.519 | 160 | 1,088 | 47,913 | 8,736 | 0 | 171 |
| 12 | 0.004 | 0.003 | 962 | 404 | 44,905 | 8,709 | 2,900 | 5,709 |
| 13 | 4.515 | 4.516 | 4,669 | 3,914 | 3,009 | 27 | 51,134 | 23,866 |
| 14 | 0.000 | 0.000 | 0 | 0 | 0 | 0 | 0 | 0 |
| 15 | 4.517 | 4.517 | 76,567 | 9,760 | 940 | 0 | 428 | 9,626 |
| 16 | 0.000 | 0.000 | 0 | 0 | 0 | 0 | 0 | 0 |
| 17 | 4.517 | 4.517 | 76,567 | 9,760 | 940 | 0 | 428 | 9,626 |
| 18 | 0.002 | 0.001 | 77,369 | 22,684 | 2,664 | 24 | 3,328 | 15,164 |
| 19 | 0.000 | 0.000 | 0 | 0 | 0 | 0 | 0 | 0 |
| 20 | 0.004 | 0.003 | 962 | 404 | 49,638 | 8,760 | 2,900 | 5,709 |
| 21 | 0.00 | 0.00 | 0 | 13,608 | 0 | 0 | 0 | 0 |

TABLE 14B

Extractor Column Design Parameters

| | S/F Ratio | W/S Ratio | Stages | Diam. (M) | % Ru Recov | Total Flow, (kg/hr) | EG Prod. (kg/hr) | % EG Glycolates to Back Extr | Heptane Distilled, (kg/hr) |
|---|---|---|---|---|---|---|---|---|---|
| Fwd | 0.70 | 0.20 | 12 | 2.8 | 99.95% | 179,310 | 77,369 | 100% | 0 |
| Back | 1.59 | | 10 | 2.5 | 99.92% | 150,217 | | | |

Example 19

This example illustrates a computer-generated material balance for an embodiment of the instant invention that can be illustrated by FIG. 4 for the extractive recovery of the BuO-triphos Ru catalyst from a glycolic acid hydrogenation effluent as exemplified in Example 8. Stream ID's are as shown in FIG. 4. The solvent stream 20 for the forward extraction is 15 weight percent heptane in 2-ethylhexanol at a solvent to feed ratio of 1.5. Water wash enters Forward Extractor 1 via stream 21 at a ratio of 0.2 kg per kg of solvent. The feed substrate solvent stream 10 for the back extraction is a mixture of glycolate esters of ethylene glycol as exemplified in Example 11 and by the glycolic acid/ester extractant mixture described above. The system was modeled using the Kremser method, as described in Treybal, *Liquid Extraction*, $2^{nd}$ Ed., McGraw Hill, 1963, pp. 248-252, for both the forward and back extractions, with partition coefficients correlated from the data of Examples 7 and 11. Material balance data is given in Table 15A. No heptane was added to the extract stream 11 of Forward Extractor 1. The reaction product stream 18 comprises 77,369 kg/hr of ethylene glycol. A summary of the resulting extractor column design parameters are given in Table 15B.

TABLE 15A

Calculated Material Balances for a Recovery Process Illustrated by FIG. 4 (All values in kg/hr)

| Stream ID | Ru | P | EG | H$_2$O | 2-EH | Heptane | EG glycolates | Other Polar Compunds |
|---|---|---|---|---|---|---|---|---|
| 10 | 0.000 | 0.000 | 5,471 | 3,230 | 0 | 0 | 54,034 | 10,322 |
| 11 | 4.515 | 4.514 | 292 | 3,056 | 123,358 | 21,884 | 0 | 366 |
| 12 | 0.000 | 0.000 | 2,470 | 1,047 | 120,332 | 21,857 | 7,561 | 11,834 |
| 13 | 4.514 | 4.513 | 3,293 | 5,239 | 3,027 | 27 | 46,474 | 17,936 |
| 14 | 0.000 | 0.000 | 0 | 0 | 0 | 0 | 0 | 0 |
| 15 | 4.517 | 4.517 | 76,567 | 9,760 | 940 | 0 | 428 | 9,626 |
| 16 | 0.000 | 0.000 | 0 | 0 | 0 | 0 | 0 | 0 |
| 17 | 4.517 | 4.517 | 76,567 | 9,760 | 940 | 0 | 428 | 9,626 |
| 18 | 0.002 | 0.003 | 78,746 | 41,295 | 1,677 | 15 | 7,988 | 21,094 |
| 19 | 0.000 | 0.000 | 0 | 0 | 0 | 0 | 0 | 0 |
| 20 | 0.000 | 0.000 | 2,470 | 1,047 | 124,095 | 21,899 | 7,561 | 11,834 |
| 21 | 0.00 | 0.00 | 0 | 33,544 | 0 | 0 | 0 | 0 |

TABLE 15B

Extractor Column Design Parameters

| | S/F Ratio | W/S Ratio | Stages | Diam. (M) | % Ru Recov | Total Flow, (kg/hr) | EG Prod. (kg/hr) | % EG Glycolates to Back Extr | Heptane Distilled, (kg/hr) |
|---|---|---|---|---|---|---|---|---|---|
| Fwd | 1.74 | 0.20 | 12 | 3.7 | 99.95% | 299,779 | 78,746 | 100% | 0 |
| Back | 0.62 | | 5 | 3.3 | 99.99% | 241,104 | | | |

The invention claimed is:

1. A process for recovering a homogeneous catalyst, comprising (A) contacting an aqueous mixture comprising glycolic acid, glycolate esters, methyl glycolate, oligomers of glycolic acid, or mixtures thereof, with hydrogen in the presence of a catalyst composition comprising ruthenium and tris-1,1,1-(diphenylphosphinomethyl)ethane to form a glycolic acid hydrogenation product comprising about 50 to about 90 weight percent, based on the total weight of said glycolic acid hydrogenation product, ethylene glycol, about 0.5 to about 25 weight percent water, and about 0.5 to about 30 weight percent of one or more reaction by-products selected from glycolic acid, oligomers of glycolic acid, and glycolate esters of ethylene glycol, and said catalyst composition;

(B) extracting said glycolic acid hydrogenation product with a first extractant, comprising about 60 to 100 weight percent, based on the total weight of said first extractant, 2-ethylhexanol and about 0 to about 40 weight percent of a hydrocarbon having 5 to 20 carbon atoms to form a first raffinate phase comprising a major amount of said ethylene glycol contained in said glycolic acid hydrogenation product and a first extract phase comprising a major amount of said catalyst composition contained in said glycolic acid hydrogenation product;

(C) separating said first raffinate and extract phases;

(D) extracting said first extract phase from step (C) with a second extractant comprising water, ethylene glycol, glycolate esters of ethylene glycol, glycolic acid, glycolic acid oligomers, or mixtures thereof to form a second extract phase comprising a major amount of said catalyst composition contained in said first extract phase from step (C) and a second raffinate phase comprising a minor amount of said catalyst composition contained in said first extract phase; and (E) combining said second extract phase with said aqueous mixture of glycolic acid of step (A).

2. The process according to claim 1 further comprising combining said second raffinate phase of step (D) with said first extractant of step (B), or distilling said second raffinate phase of step (D) to produce a hydrophobic solvent distillate and combining said hydrophobic solvent distillate with said first extractant of step (B).

3. The process according to claim 1 wherein said hydrocarbon is selected from hexane, heptane, octane, decane, benzene, toluene, xylenes, methyl napththalenes, isoparaffinic mixed hydrocarbons having a boiling range between 90 and 325° C., and mixtures thereof.

4. The process according to claim 1 wherein said first extractant comprises a hydrophilic solvent selected from water, ethylene glycol, glycolic acid, oligomers of glycolic acid, glycolate esters, and mixtures thereof.

5. The process according to claim 1 wherein said hydrocarbon comprises heptane.

6. The process according to claim 1 wherein said second extractant comprises mono-and diglycolate esters of ethylene glycol.

7. The process according to claim 6 wherein said hydrocarbon comprises heptane.

8. The process according to claim 1 wherein said steps (B), (D), or (B) and (D) are carried out by fractional countercurrent extraction.

* * * * *